United States Patent [19]
Au-Young et al.

[11] Patent Number: 5,783,418
[45] Date of Patent: Jul. 21, 1998

[54] HUMAN HOMOLOG OF THE RAT G PROTEIN GAMMA-5 SUBUNIT

[75] Inventors: Janice Au-Young, Berkeley; Susan G. Stuart, Montara; Lynn E. Murry, Portola Valley; Karl J. Guegler, Menlo Park; Jeffrey J. Seilhamer, Los Altos Hills, all of Calif.

[73] Assignee: Incyte Pharmaceuticals, Inc., Palo Alto, Calif.

[21] Appl. No.: 606,789

[22] Filed: Feb. 27, 1996

Related U.S. Application Data

[63] Continuation-in-part of Ser. No. 440,743, Jun. 12, 1995, which is a continuation-in-part of Ser. No. 320,011, Oct. 5, 1994.

[51] Int. Cl.$^6$ .............................. C12N 15/12; C12N 15/63; C12N 15/85
[52] U.S. Cl. ...................... 435/69.1; 435/320.1; 435/325; 536/23.2
[58] Field of Search .............................. 536/23.5, 23.2; 435/320.1, 240.2, 69.1, 325

[56] References Cited

PUBLICATIONS

Fisher KJ, et al. "Characterization of the cDNA and genomic sequence of a G protein gamma subunit (gamma 5)." Mol. Cell. Biol. 12: 1585–1591 Apr. 1992.

Sambrook J, et al. "Molecular Cloning: A Laboratory Manual." Cold Spring Harbor Laboratory Press, NY. 1989.
Aussel et al., J. Immunol., pp. 140:215–220 (1988).
Clapman et al., New Roles for G–protein βγ–dimers in transmembrane signaling, Nature, 365:403–406, (1993).
Fisher et al., Characterization of the cDNA and Genomic Sequence of a G Protein γSubunit (γ5), Mol. Cell. Biol., 12:1585–1591 (1992).
Iyengar, Molecular and functional diversity of mammalian G–stimulated adenylyl cyclases.FASEB Jour., 7:768–775, (1993).
Neer et al., Heterotrimeric G Proteins: Organizers of Transmembranes Signals, Cell, 80:249–257 (1995).
Stephens et al., A Novel Phosphoinositide 3 Kinase Activity in Myeloid–Derived Cells is Activated by G Protein βγSubunits, Cell, 77:83–93 (1994).
Watson et al., The G protein Linked Receptor Facts Book, pp. 350–355 (1994).

Primary Examiner—Douglas W. Robinson
Assistant Examiner—Amy J. Nelson
Attorney, Agent, or Firm—Lucy J. Billings

[57] ABSTRACT

The present invention provides a nucleic acid sequence which identifies and encodes a G protein gamma subunit (gpg) which was isolated from human pituitary gland. The invention provides for genetically engineered expression vectors and host cells comprising nucleic acid sequence encoding GPG. The invention also provides for purified GPG.

4 Claims, 9 Drawing Sheets

```
                9           18           27           36           45           54
5' ATG TCT GGC TCC TCC AGC GTC GCC GCT ATG AAG AAA GTG GTT CAA CAG CTC CGG
   M   S   G   S   S   S   V   A   A   M   K   K   V   V   Q   Q   L   R 63           72           81           90           99          108
   CTG GAG GCC GGA CTC AAC CGC GTA AAA GTT TCC CAG GCA GCT GCA GAC TTG AAA
   L   E   A   G   L   N   R   V   K   V   S   Q   A   A   A   D   L   K 117          126          135          144          153          162
   CAG TTC TGT CTG CAG AAT GCT CAA CAT GAC CCT CTG CTG ACT GGA GTA TCT TCA
   Q   F   C   L   Q   N   A   Q   H   D   P   L   L   T   G   V   S   S 171          180          189          198          207          216
   AGT ACA AAT CCC TTC AGA CCC CAG AAA GTC TGT TCC TTT TTG TAG TAA AAT GAA
   S   T   N   P   F   R   P   Q   K   V   C   S   F   L   *   *   N   E 225          234          243
   TCT TTC AAA GGT TTC CCA AAC CAC TCC TTA TGA 3'
   S   F   K   G   F   P   N   H   S   L   *
```

FIGURE 1

```
 40 GTCTGGCCCCGCCGACCCACGGCCCACGACCCACCGACCCACGAATCGGC  89
    | |||||||  ||  ||||||   ||  ||    ||  ||   || ||  ||| ||
  6 GACTGGCCCAGCGGACCCATCGCAGACCTGCCGACGGCCCGCGGATCTGC  55

90 CCGGCCGTCGCGTGCACCATGTCTGGCTCCTCCAGCGTCGCCGCTATGAA 139
    |    |   |||  ||||  ||||||||||| || ||||||||||| |||||||||
 56 CATCCTTTCGAGTGCGCCATGTCTGGTTCATCCAGCGTCGCGGCTATGAA 105

140 GAAAGTGGTTCAACAGCTCCGGCTGGAGGCCGGACTCAACCGCGTAAAAG 189
    ||||||||||||||||||||||||||||||||||| |||||  ||  || ||  |
106 AAAAGTGGTTCAACAGCTCCGGCTGGAGGCCGGGCTCAATCGGGTGAAGG 155

190 TTTCCCAGGCAGCTGCAGACTTGAAACAGTTCTGTCTGCAGAATGCTCAA 239
    ||||||||||||||||||| ||||||||||||||||||||||||||||||
156 TTTCCCAGGCAGCTGCAGATTTGAAACAGTTCTGTCTGCAGAATGCTCAA 205

240 CATGACCCTCTGCTGACTGGAGTATCTTCAAGTACAAATCCCTTCAGACC 289
    ||||||||||||||||||||||||||||||||||||||||||||||| ||
206 CATGACCCTCTGCTGACTGGAGTATCTTCAAGTACAAATCCCTTCAGGCC 255

290 CCAGAAAGTCTGTTCCTTTTTGTAGTAAAATGAATCTTTCAAAGGTTTCC 339
    |||||||||||||||||||||||||||| | |||||||   ||||||| |
256 CCAGAAAGTCTGTTCCTTTTTGTAGTAAGACGAATCTTGACAAGGTTTTC 305

306 CAAACCACTCCTTATGATCCAGTGAATATTCAAGAGGA.GCTACATTTGA 388
    ||||||||   |  |||   ||||||||||||||||   |  | |||| ||||||
389 CAAACCACGTTTCATAAACCAGTGAATATTCAAAGGAAAGCTAAATTTGA 355

356 AGCCT 393
    |||||
356 AGCCT 360
```

| | | |
|---|---|---|
| 296 | A G T C T G T T C C T T T T T T G T A G T A A A A T G A A T C T T T C A A A G G T T T C C C A A A C C | 112530.pitunct01 |
| 136 | G G G T A A T T - - G T T T T A T A - T A C A C T G G - - - - C A G C A G C N T N C A A T A A A | n183288.cardnot01 |
| 137 | G G G T A A T T - - G T T T T A T A - T A C A C T G G - - - - C A G C A G C A T A C A A T A A A | n206842.splnnot02 |
| 137 | - - - A G T T - - G C T C - - - - - A G - - - - - C A G C A G C T T - - T A T T | n211765.splnnot02 |
| 162 | G G G T A A T T - - G T T T T A T A - T A C A C T G G - - - - C A G C A G C A T A N A A T A A A | n215213.stanot01 |
| 68 | G G G T A A T T - - G T T T T A T A - T A C A C T G G - - - - C A G C A G C A T A C A A T A A A | n215233.stanot01 |
| 235 | A A A A - G C T T A T C C C T G T A A C A C A - - - T G T G C C A T A A - T A T A C A A A C T | n286874.eosihet02 |
| 289 | | | n292714.tmlr3dt1 |
| 230 | | | n352443.lvennot01 |
| 248 | | | n404483.tmlr3dt1 |
| 143 | G A - - - - - - - - - - - - - - - - - - - - - - - G A A G T T - - - - T G C T G A G G A A T | n427016.bladnot01 |
| 188 | G G - - - - - - - - - - - - - - - - - - - - - - - G A G C C T - - - A G A T C C T G T G C T T T | n433742.thynmot01 |
| 230 | | | n439616.thynmot01 |
| 219 | | | n453899.tlymnot02 |
| 241 | | | n460437.keranot01 |
| 210 | A G T N T G T T C C T T T T T T G T A G T A A A A T G A A T C T T T C A A A G G T T T T C C A A A C C | n475026.mmlr2dt1 |
| 198 | G G - - - - - - - - - - - - - - - - - - - - - - - G A G C C C T - - - A G A T N C T G T G C | n482881.hnt2rat01 |
| 179 | | | n484339.hnt2rat01 |
| 255 | A G T N T G T | | n498118.neut1pt01 |
| 193 | | | n498822.neut1pt01 |
| 12 | G G G T A A T T - - G T T T T A T A - T A C A C T G G - - - - C A G C A G C A T A C A A T A A A | n499687.neut1pt01 |
| 206 | | | n500281.neut1pt01 |
| 271 | A G T N T G T | | n567503.mmlr3dt01 |
| 260 | | | n586994.utrsnot01 |

FIGURE 4E

FIGURE 4F ns, the dimer may regulate potassium channels, mediate mitogen-activated protein kinase pathways and activate or increase phosphoinositide hydrolysis. In yeast, the dimer mediates a G protein-dependent mating response. The five β subunit isotypes share 53-90% amino acid identity and are expressed ubiquitously although it must be noted that β-4 is more abundant in brain and lung than in other tissues (Clapman D. E. and E. J. Neer (1993) Nature 365:403–6).

HUMAN HOMOLOG OF THE RAT G PROTEIN GAMMA-5 SUBUNIT

CROSS REFERENCE TO OTHER APPLICATIONS

This is a continuation-in-part application of co-pending application Ser. No. 08/440,743, filed Jun. 12, 1995, entitled "Polynucleotides derived from Human Pituitary" which is a continuation-in-part of co-pending application Ser. No. 08/320,011 filed Oct. 5, 1994, entitled Novel Human Pituitary Cell-Derived Polynucleotides and Polypeptides, the disclosure of which is incorporated herein by reference.

FIELD OF THE INVENTION

The present invention is in the field of molecular biology; more particularly, the present invention describes the nucleic acid and amino acid sequences of a human homolog of the rat G protein gamma-5.

BACKGROUND OF THE INVENTION

The heterotrimeric G proteins, a family of GTPases, are present in all cells. They control a variety of functions (metabolic, humoral, neural and developmental) by transducing hormonal, neurotransmitter and sensory signals into an array of cellular responses. Triggered by cell surface receptors, each G protein regulates the activity of a specific effector. The effectors include adenylate cyclase, phospholipase C, and ion channel proteins which initiate appropriate biochemical responses. G proteins can exhibit strict subcellular localization and can included in endocytic vesicles (Alberts B. et al (1994) *Molecular Biology of the Cell*, Garland Publishing, Hamden Conn.).

Each G protein is composed of alpha (α), beta (β) and gamma (γ) subunits associated as a complex in the inactive, GDP-bound form. Activation of a transmembrane receptor by a hormone results in activation of the GTPase and replacement of GDP by GTP. The activated heterotrimer, the activated α subunit, or the β-γ subunit may have specific activity. Generally, the α subunit of a G protein disassociates from the β and γ complex, interacts with receptors and carries the message to the effector.

There are at least 20 genes for Gα subunits which encode four major classes of proteins with at least 56–95% amino acid identity. The stimulatory, Gs class, is sensitive to pertussis toxin which uncouples the receptor:G protein interaction. This uncoupling blocks signal transduction to those receptors that decrease the cAMP which regulates ion channels and activates phospholipases. The inhibitory, Gi class, is also susceptible to modification by pertussis toxin which prevents Gi from lowering cAMP levels. Two novel classes refractory to pertussis toxin modification, are Gq which activates phospholipase C and $G_{12}$ which has sequence homology with the Drosophila gene concertina which may contribute to the regulation of embryonic development. The Gα subunits range in molecular weight from 39–52 kDa and include some splice variants. Multiple genes also encode at least four β and six γ subunits which range in molecular weight from 35–36 kDa and 6–10 kDa, respectively (Watson S. and S. Arkinstall (1994) *The G protein Linked Receptor Facts Book*, Academic Press, San Diego Calif.).

The β-γ dimer promotes the association of the GDP-bound α subunit with ligand-bound receptor. The dimer both orients and stabilizes the association so that signal transduction does not occur in the absence of agonist. Neer E. J. (1995; Cell 80:249–257) reported that β-γ dimers interact with adenylyl cyclase, phospholipase C β, calmodulin, β adrenergic receptor kinase, phospholipase A2, phosducin, phosphoinositide 3-kinase, transducin, etc. In addition, the dimer may regulate potassium channels, mediate mitogen-activated protein kinase pathways and activate or increase phosphoinositide hydrolysis. In yeast, the dimer mediates a G protein-dependent mating response. The five β subunit isotypes share 53-90% amino acid identity and are expressed ubiquitously although it must be noted that β-4 is more abundant in brain and lung than in other tissues (Clapman D. E. and E. J. Neer (1993) Nature 365:403–6).

The known γ subunits from bovine, rat and mouse tissues are most divergent in their N-terminal sequence. The γ subunits generally display at least one cysteine residue in approximately the middle of their amino acid sequence (between residues 35 and 45) which is important for dimer formation, ie, the cysteine in the γ subunit cross links with a cysteine in the β subunit. Many of the sequences show a C-terminal consensus sequence CAAX (where A represents aliphatic residues and X is unspecified) which resembles the ras oncogene terminal sequence and is a site for post-translational modification. The modification involves cleavage of the 3' terminal residues and subsequent carboxymethylation, farnesylation, geranylgeranylation or isoprenylation. Post-translational modification increases subunit diversity and hydrophobicity and is important for membrane association and functional activity. In contrast, the rat β-5 sequence which terminates in CSFL is widely expressed and was highly expressed in kidney, heart, lung, and brain.

Although the different G proteins subunits could form some 600 different combinations, not all combinations are possible or functional. In the case of dimers, the β1-γ1 is only active in retina. Furthermore, the pattern of effector regulation may be highly specific. For example, whereas one type of adenylyl cyclase is activated by the Gα subunit and unaffected by the B-β subunit, a second type is activated by a subunit and inhibited by β-γ subunit. In another example involving the pituitary-derived GH3 cell line, the somatostatin receptor and the muscarinic receptor both regulate calcium channels, but each uses an alternatively spliced form of the $α_{s/o}$ and different β-γ subunits. A final example addresses specificity and efficiency; in reconstituted vesicles, the β-adrenergic receptor activates Gs as much as 3-fold better than Gi and the β-γ subunits from either heterotrimer should activate the potassium channel, however, only adenylyl cyclase is activated.

Neer (supra) suggests that G protein regulation depends on a combination of factors including the kinetics of ATP hydrolysis, stoichiometry, covalent modification, accessory proteins and compartmentalization, and that the number of receptors exceeds the number of G proteins. The molecular and functional diversity of Gs-stimulated adenylyl cyclases was recently reviewed by Iyengar R. (1993; FASEB Jour 7:768–75), and different tissues were shown to express a variety of adenylyl cyclases which were differentially regulated by the β-γ dimers and other molecules.

Diseases Associated with Cell Signaling Molecules and Pathways

Mutations in the molecules and alterations in the expression pattern of the components of the cell signaling cascade may result in abnormal activation of leukocytes or lymphocytes or cellular proliferation which affects growth and development. Inappropriate activation of leukocytes or lymphocytes may result in the tissue damage and destruction seen in autoimmune diseases such as rheumatoid arthritis, biliary cirrhosis, hemolytic anemia, lupus erythematosus, and thyroiditis. For example, Aussel C. et al. (1988; J Immunol 140–215) reported that T cell activation is a G protein regulated process. Work in Jurkat cells with pertussis toxin showed that G protein serves as a transducer for signals via the T cell receptor-CD3 complex. In addition, the fact that fluoride ions stimulate the release of diacylglycerol but not inositol phosphate 3 further suggests that G proteins control the activity of phospholipase C.

Abnormal proliferation of cells can cause endometriosis or tumors, adenomas or carcinomas. Cyclic AMP stimulation of brain, thyroid, adrenal, and gonadal tissue proliferation is regulated by G proteins. In fact, about 50 percent of growth hormone-producing pituitary adenomas contain a mutated $G\alpha_s$ allele, and similar mutations have been associated with thyroid carcinomas and the neoplastic lesions of McCune-Albright syndrome. A known mutation in the $G\alpha_{2i}$ gene is found in tumors derived from adrenal cortex and ovary. Persistent extracellular stimulation and expression of those receptors coupled to Gq and phospholipase C can also result in tumor formation (Isselbacher K. J. et al (1994) Harrison's Principles of Internal Medicine, McGraw-Hill, New York N.Y.). In addition, multiple endocrine hyperfunction may be due to defects in the G protein-cyclic AMP-protein kinase A-dependent pathway.

Phosphoinositide 3 kinase is a key signaling enzyme implicated in receptor stimulated mitogenesis, oxidative bursting in neutrophils, membrane ruffling and glucose uptake. Stephens L. et al. (1994; Cell 77:83–93) report that phosphoinositide 3 kinase activation in myeloid derived cells is regulated by $\beta$-$\gamma$ dimers as well as phosphotyrosine kinase. Furthermore, it appears that tissue specificity may be governed by concentration of $\beta$-$\gamma$ dimer molecules and that activation is more rapid and transient than that regulated by phosphotyrosine kinase. Although it was not suggested, it appears that the ability to control expression of either $\beta$ or $\gamma$ subunits provides a means to regulate cell signaling and mitogenesis.

The diversity of G subunit proteins, their functional combinations and their interactions with receptors present opportunities to intercede in abnormal cell processes. The activation of G proteins and the rate of GTP hydrolysis can be altered by controlling subunit production and association. Preventing dimer and heterotrimer formation can diminish cell signalling in GTP regulated pathways, reducing the activation of second messengers and controlling activation of leukocytes and lymphocytes and cell proliferation associated with endometriosis and tumor formation.

SUMMARY

The present invention relates to a novel G protein gamma subunit, GPG, whose nucleic acid sequence, gpg, was identified among the polynucleotides of a human pituitary library and to the use of the nucleic acid and amino acid sequences in the study, diagnosis, prevention and treatment of disease.

The novel polynucleotide encoding GPG was first identified in Incyte Clone No. 112530 through a computer generated search for nucleotide sequence alignments. The clone was resequenced, and the coding region determined. The nucleotide sequence (SEQ ID NO:1) encodes a protein of 68 amino acids (SEQ ID NO:2). Significant features of the novel GPG are the presence of the $C_{38}$ linking residue and the presence of the C-terminal CAAX motif. Other G protein sequences (SEQ ID NOs:9–31) presented in the Sequence Listing are exact matches, related sequences or variants of SEQ ID NO:1.

The present invention and its use is based, in part, on the fact that GPG is most closely related to the rat G protein $\gamma$-5 subunit. It is also based on the tissue distribution of the exact matches, related sequences or variants of SEQ ID NO:1 which were found in uterus, thyroid, T cell, stomach, spleen, keratinocyte, eosinophil, cardiac, bladder, and stimulated macrophage, neuronal, and neutrophil libraries.

The use of GPG, and of the nucleic acid sequences which encode it, is also based on the amino acid and structural homologies between GPG and the other known G protein $\gamma$ subunits as well as on the known associations and functions of heterotrimeric and dimeric G proteins. The timing of and amount of expression of GPG is implicated in activation of leukocytes or lymphocytes in autoimmune diseases such as rheumatoid arthritis, biliary cirrhosis, hemolytic anemia, lupus erythematosus, and thyroiditis and in cell proliferation associated with endometriosis or with the formation of tumors of brain, thyroid, adrenal, and gonadal tissues.

The gpg polynucleotide sequence, oligonucleotides, fragments, portions or antisense molecules thereof, may be used in diagnostic assays to detect and quantify levels of gpg mRNA in cells and tissues. For example, gpg polynucleotides, or fragments thereof, may be used in hybridization assays of body fluids or biopsied tissues to detect the level of gpg expression.

The present invention also relates, in part, to an expression vector and host cells comprising nucleic acids encoding GPG. Such transfected host cells are useful for the production and recovery of GPG. The present invention also encompasses purified GPG.

The invention further provides diagnostic kits for the detection of naturally occurring GPG and provides for the use of purified GPG as a positive control and to produce anti-GPG antibodies. These antibodies may be used to monitor GPG expression conditions or diseases associated with activation of leukocytes or lymphocytes or with cell proliferation in endometriosis or tumor formation.

The invention further provides for methods for treatment of conditions or diseases associated with overexpression of GPG by the delivery of effective amounts of antisense molecules, including peptide nucleic acids, or inhibitors of GPG for the purpose of diminishing leukocyte or lymphocyte activation, particularly in autoimmune diseases, or preventing cell proliferation in endometriosis or growing tumors.

The invention also provides pharmaceutical compositions comprising vectors containing antisense sequences or inhibitors of GPG which can be used in the prevention or treatment of conditions or diseases including, but not limited to, excessive leukocyte or lymphocyte activation or cell proliferation. For example, specific GPG inhibitors can be used to prevent dimer and/or heterotrimer formation thus moderating leukocyte or lymphocyte activation in the joints of individuals subject to rheumatoid arthritis or slowing cell proliferation associated with tumor formation in endocrine tissues.

DESCRIPTION OF THE FIGURES

FIG. 1 displays the nucleic acid sequence (SEQ ID NO:1) and deduced amino acid sequence (SEQ ID NO:2) of a G protein gamma subunit (GPG) from human pituitary gland. The alignment of the nucleic acid and amino acid sequences were produced using MacDNAsis (Hitachi Software Engineering Ltd).

FIG. 2 shows the nucleotide sequence identity between gpg and the bovine G protein gamma 5 subunit. Sequences were aligned using the ABI INHERIT™ 670 Sequence Analysis System (Perkin Elmer, Norwalk Conn.).

Figure 3:
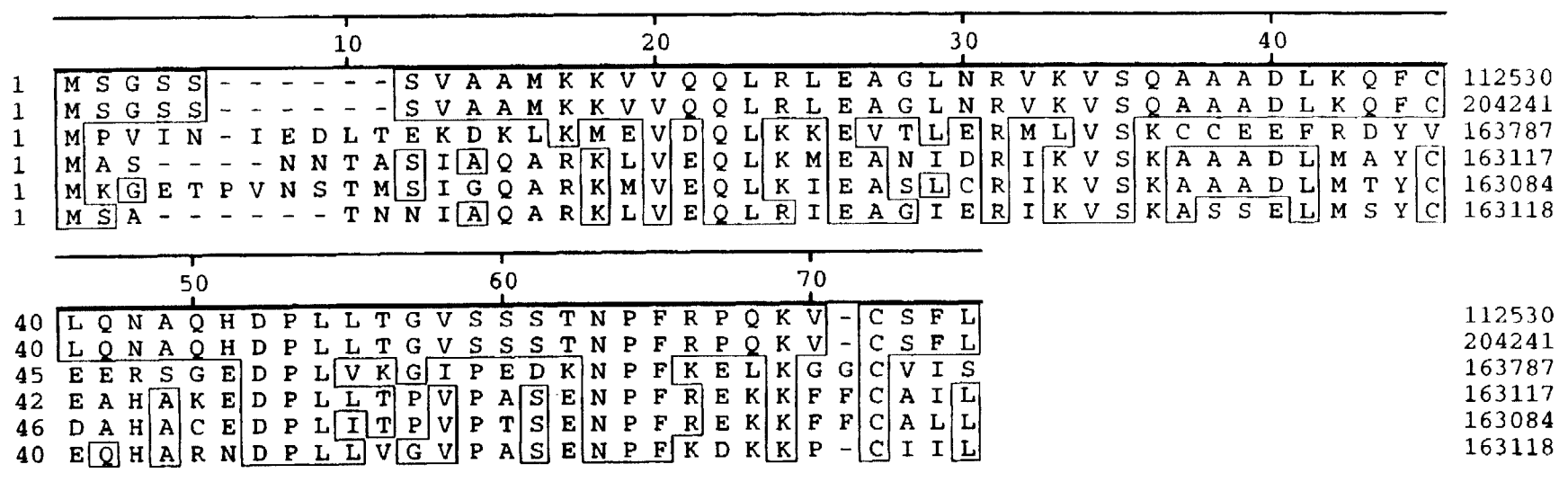

FIG. 3 shows the amino acid sequence alignment between GPG, rat G protein γ-5 subunit (GI 204241; SEQ ID NO:3), bovine G protein γ-1 subunit (GI 163787; SEQ ID NO:4), bovine G protein γ-2 subunit (GI 163117; SEQ ID NO:5), bovine G protein γ-3 subunit (GI 163084; SEQ ID NO:6), and bovine G protein γ-7 subunit (GI 163118 (translated); SEQ ID NO:7). Sequences were aligned using the multisequence alignment program of DNASTAR software (DNASTAR Inc, Madison Wis.).

FIGS. 4A–4F show the nucleotide sequence alignment of SEQ ID NO:1 with the other exact matches, related sequences, or variants of gpg, SEQ ID NOs:9–31, which are presented in the sequence listing. The open reading frame for these molecules starts at nucleotide $A_{110}$ and for Incyte Clone 112530 ends at $T_{314}$. Sequences were aligned using the multisequence alignment program of DNASTAR software.

DETAILED DESCRIPTION OF THE INVENTION

The present invention relates to a novel G protein gamma subunit whose nucleic acid sequence was identified among the polynucleotides of a human pituitary library (PITUNOT01) and to the use of the nucleic acid and amino acid sequences in the study, diagnosis, prevention and treatment of disease. As used herein, the abbreviation for the novel G protein gamma subunit in lower case (gpg) refers to a nucleic acid sequence, while the upper case (GPG) refers to an amino acid sequence.

The polynucleotide sequence (FIG. 1) encoding GPG was first identified within Incyte Clone No. 112530. A BLAST search (Basic Local Alignment Search Tool; Altschul S. F. (1993) J Mol Evol 36:290–300; Altschul S. F. et al (1990) J Mol Biol 215:403–10) comparing the cDNAs of the PITUNOT01 library against the rodent database of GenBank 90 identified Incyte Clone 112530 as a nonexact homolog of rat G protein γ-5 subunit from rat liver tissue (GI 204240; Fisher K. J. and N. N. Aronson (1992) Mol Cell Biol 12:1585–91). The nucleotide sequence of Incyte Clone 112530 was resequenced to confirm the nucleotide sequence and recompared with the sequence of rat G protein γ-5 subunit with which it shows 85% identity (FIG. 2).

Figure 4A:
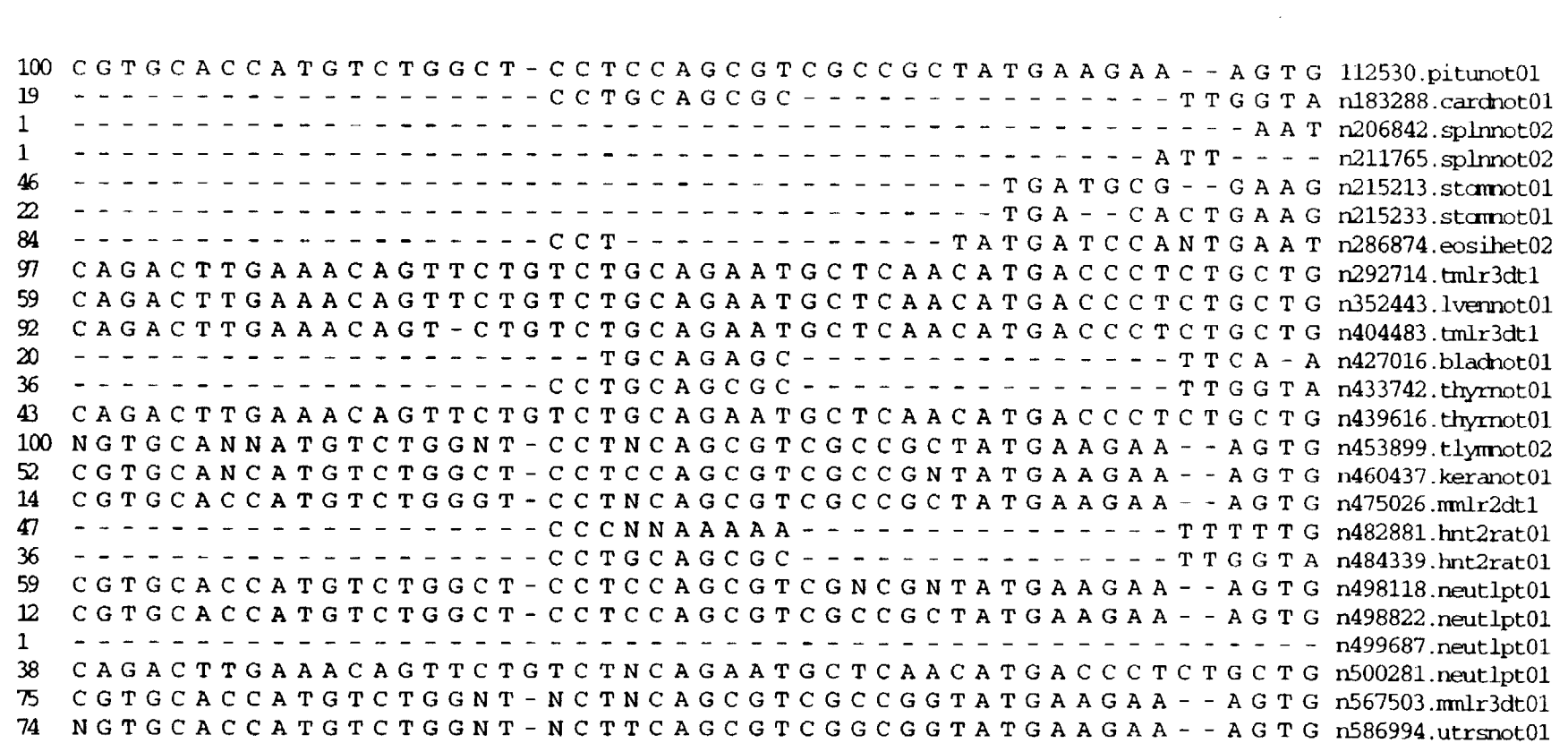
Figure 4B:
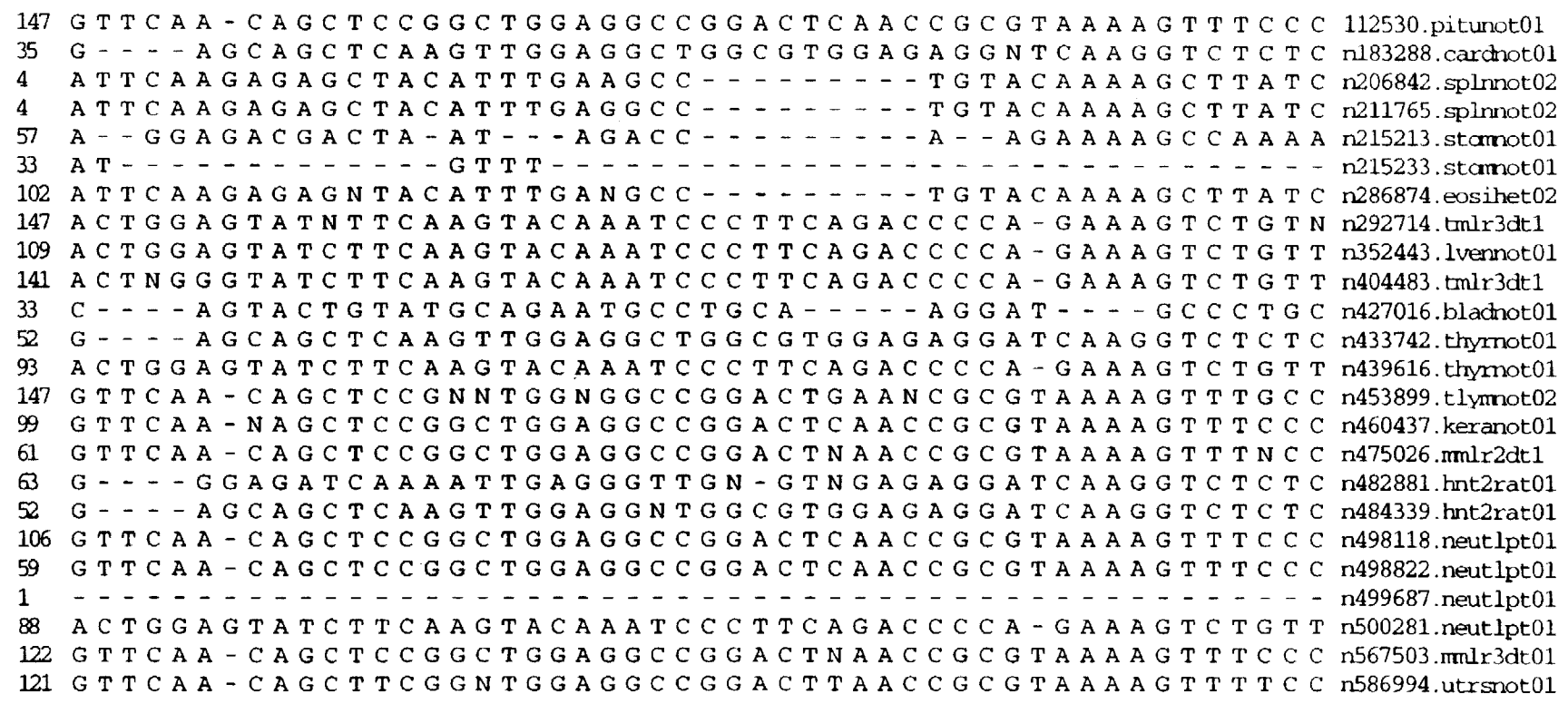
Figure 4C:
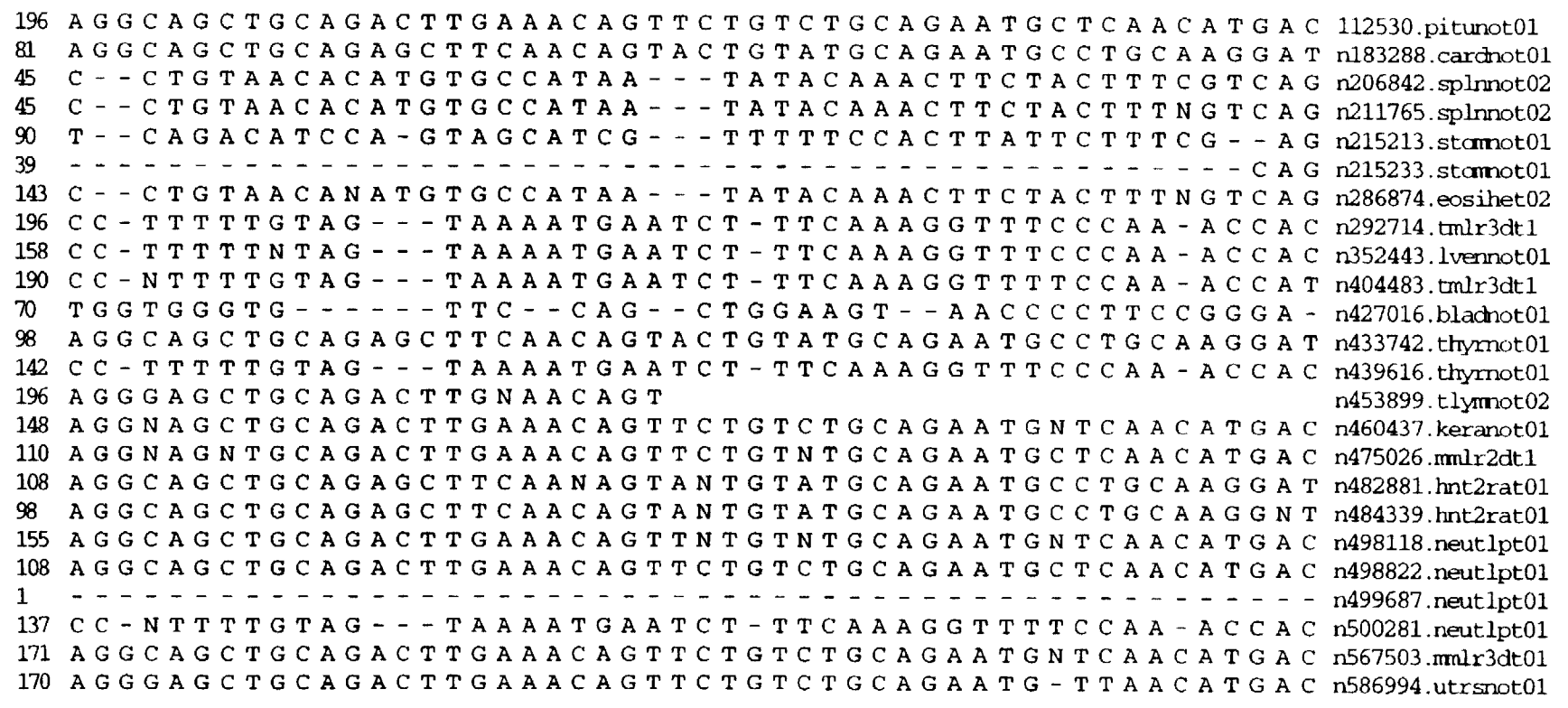
Figure 4D:
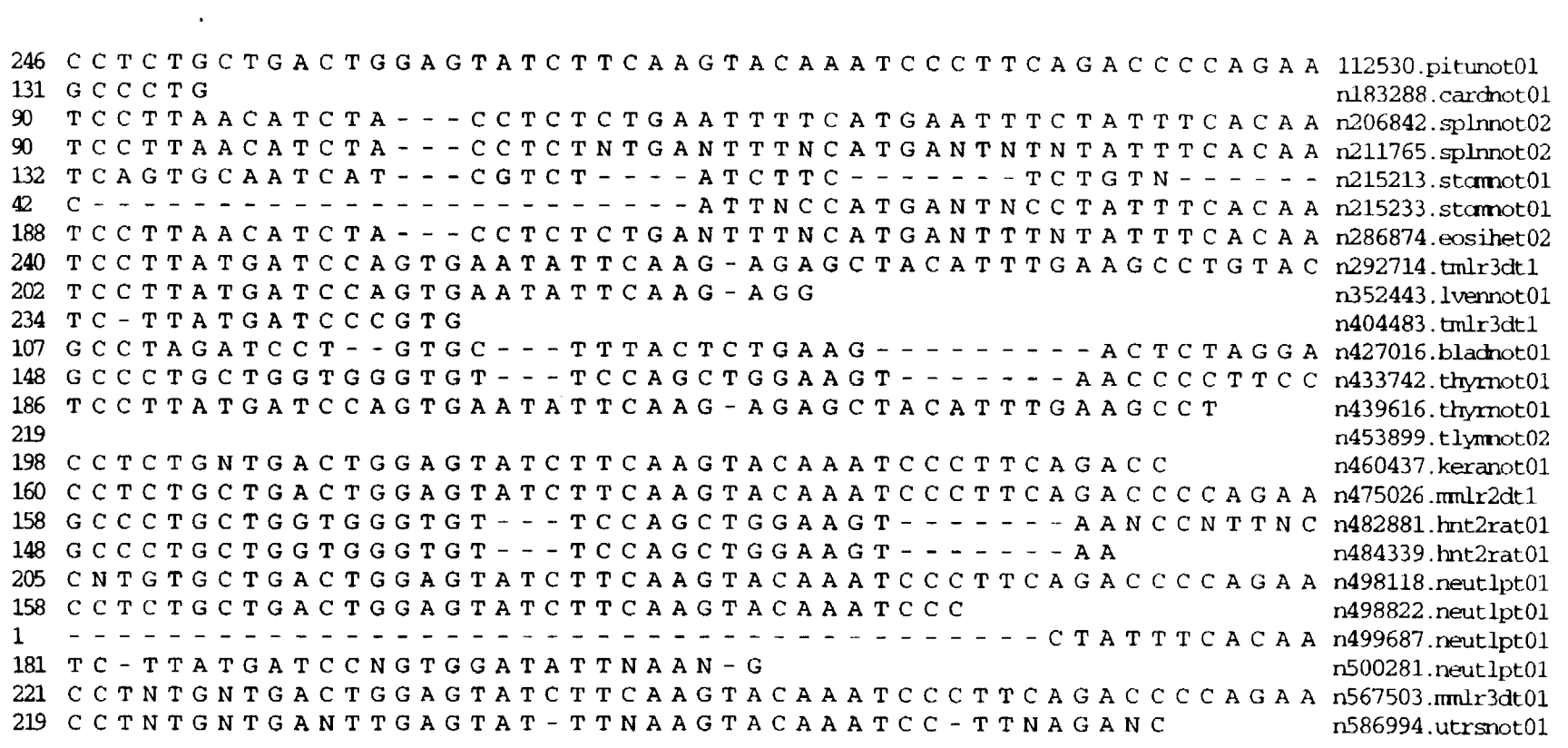
Figure 4F:
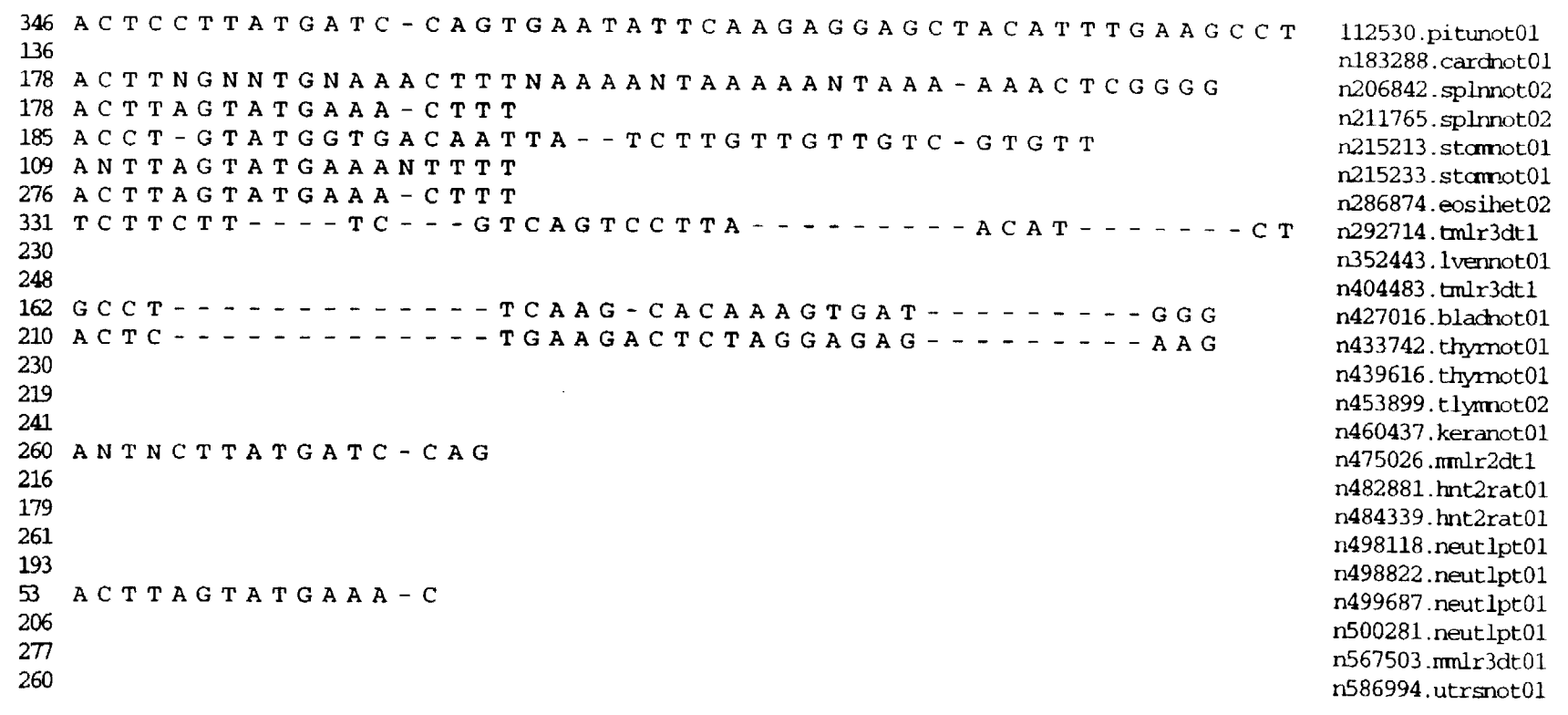

The relationships among the G protein subunits identified in Watson and Arkinstall (supra), one to another, is shown by alignment of their amino acid sequences in FIG. 2: GPG (SEQ ID:2), rat G protein γ-5 subunit (GI 204241; SEQ ID NO:3), bovine G protein γ-1 subunit (GI 163787; SEQ ID NO:4), bovine G protein γ-2 subunit (GI 163117; SEQ ID NO:5), bovine G protein γ-3 subunit (GI 163084; SEQ ID NO:6), and bovine G protein γ-7 subunit (GI 163118 (translation); SEQ ID NO:7). As can be seen in FIG. 2, the amino acid residues are conserved between GPG and the bovine G protein γ-5 subunit and the residues $M_1$, $V_{14}$, $Q_{16}$, $L_{17}$, $E_{20}$, $R_{25}$, $V_{28}$, $S_{29}$, $D_{46}$, $P_{47}$, $L_{48}$, $N_{57}$, $P_{58}$, $F_{59}$, $K_{63}$, and $C_{65}$ are conserved among G proteins known in the art. Other G protein sequences (SEQ ID NOs:9–31) presented in the Sequence Listing and in FIG. 4 are exact matches, related sequences or variants of SEQ ID NO:1.

The present invention and the use of GPG, and of the nucleic acid sequences which encode it, is based, in part, on the amino acid homology between GPG and the rat G protein γ subunit from rat liver tissue (Fisher K. J. and N. N. Aronson (1992) Mol Cell Biol 12:1585–91). It is also based on the tissue distribution of variant, closely related or exact cDNA sequences in uterus, neonatal keratinocytes, T cells, neutrophils, and stimulated macrophages, and on the known associations and functions of heterotrimeric and dimeric G proteins. Given the tissue distribution (α2 in lymphocytes and tumor cell lines; α11, in brain, and α16, in hematopoietic cells; β4, in brain and reproductive tissues) and functions of known G protein subunits, the GPG of this application is surely involved in activation of leukocytes or lymphocytes and in cell proliferation associated with endometriosis or tumor formation in endocrine hormone stimulated or producing brain, thyroid, adrenal, or gonadal tissues.

The gpg polynucleotide sequence, oligonucleotides, fragments, portions or antisense thereof, may be used in diagnostic assays to detect and quantify levels of gpg mRNA in cells and tissues. For example, gpg polynucleotides, or fragments thereof, may be used in hybridization assays of body fluids or biopsied tissues to detect the level of gpg expression.

The present invention also relates, in part, to an expression vector and host cells comprising nucleic acids encoding GPG. Such transfected host cells are useful for the production and recovery of GPG. The present invention also encompasses purified GPG.

The invention further provides diagnostic kits for the detection of naturally occurring GPG and provides for the use of purified GPG as a positive control and to produce anti-GPG antibodies. These antibodies may be used to monitor GPG expression in conditions or diseases associated with activation of leukocytes or lymphocytes or with cell proliferation in endometriosis or tumor formation.

The invention further provides for methods for treatment of conditions or diseases associated with overexpression of GPG by the delivery of effective amounts of antisense molecules, including peptide nucleic acids, or inhibitors of GPG for the purpose of diminishing leukocyte or lymphocyte activation, particularly in autoimmune diseases such as rheumatoid arthritis, biliary cirrhosis, hemolytic anemia, lupus erythematosus, and thyroiditis, or preventing cell proliferation in endometriosis or growing tumors of endocrine tissues.

The invention also provides pharmaceutical compositions comprising vectors containing antisense molecules or inhibitors of GPG which can be used in the prevention or treatment of conditions or diseases including, but not limited to, excessive leukocyte or lymphocyte activation or cell proliferation. For example, specific GPG inhibitors can be used to prevent dimer and/or heterotrimer formation thus moderating leukocyte or lymphocyte activation in the joints of individuals subject to rheumatoid arthritis or slowing cell proliferation associated with tumor formation in endocrine tissues. "Nucleic acid sequence" as used herein refers to an oligonucleotide, nucleotide or polynucleotide sequence, and fragments or portions thereof, and to DNA or RNA of genomic or synthetic origin which may be single- or double-stranded, and represent the sense or antisense strand. Similarly, amino acid sequence as used herein refers to an oligopeptide, peptide, polypeptide or protein sequence. "Peptide nucleic acid" as used herein refers to a molecule which comprises an antisense oligomer to which an amino acid residue, such as lysine, and an amino group have been added. These small molecules, also designated anti-gene agents, stop transcript elongation by binding to their complementary (template) strand of DNA (Nielsen P. E. et al (1993) Anticancer Drug Des 8:53–63).

As used herein, GPG refers to the amino acid sequence of GPG from any species, including, bovine, ovine, porcine, equine, murine and preferably human, in a naturally occurring form or from any source, whether natural, synthetic, semi-synthetic or recombinant. As used herein, "naturally occurring" refers to a molecule, nucleic acid or amino acid sequence, found in nature.

The present invention also encompasses GPG variants. A preferred GPG variant is one having at least 80% amino acid sequence similarity, a more preferred GPG variant is one having at least 90% amino acid sequence similarity and a most preferred GPG variant is one having at least 95% amino acid sequence similarity to the GPG amino acid sequence (SEQ ID NO:2). A "variant" of GPG may have an amino acid sequence that is different by one or more amino acid "substitutions". The variant may have "conservative" changes, wherein a substituted amino acid has similar structural or chemical properties, eg. replacement of leucine with isoleucine. More rarely, a variant may have "nonconservative" changes, eg. replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to a gpg having structural, regulatory or biochemical functions of the naturally occurring GPG. Likewise, "immunologically active" defines the capability of the natural, recombinant or synthetic GPG, or any oligopeptide thereof, to induce a specific immune response in appropriate animals or cells and to bind with specific antibodies. The term "derivative" as used herein refers to the chemical modification of a gpg or the encoded GPG. Illustrative of such modifications would be replacement of hydrogen by an alkyl, acyl, or amino group. A gpg derivative would encode a polypeptide which retains essential biological characteristics of a G protein g subunit such as, for example, association with a β subunit to form of a functional dimer.

As used herein, the term "purified" refers to molecules, either nucleic or amino acid sequences, that are removed from their natural environment and isolated or separated from at least one other component with which they are naturally associated.

The GPG Coding Sequences

The nucleic and deduced amino acid sequences of GPG are shown in FIG. 1. In accordance with the invention, any nucleotide sequence which encodes the amino acid sequence of GPG can be used to generate recombinant molecules which express GPG. In a specific embodiment described herein, gpg was first isolated and identified within Incyte Clone 112530 from the human pituitary library (PITUNOT01), patent application Ser. No. 08/320,011, "Novel Human Pituitary Cell Derived Polynucleotides and Polypeptides", by Seilhamer et al, filed Oct. 10, 1994, and hereby incorporated by reference.

Methods for DNA sequencing are well known in the art and employ such enzymes as the Klenow fragment of DNA polymerase I Sequenase® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.) Methods to extend the DNA from an oligonucleotide primer annealed to the DNA template of interest have been developed for both single-stranded and double-stranded templates. Chain termination reaction products were separated using electrophoresis and detected via their incorporated, labelled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; MJ Research, Watertown Mass.) and the ABI Catalyst 800 and 377 and 373 DNA sequencers (Perkin Elmer).

The quality of any particular cDNA library may be determined by performing a pilot scale analysis of the cDNAs and checking for percentages of clones containing vector, lambda or *E. coli* DNA, mitochondrial or repetitive DNA, and clones with exact or homologous matches to public databases.

Extending the Polynucleotide Sequence

The polynucleotide sequence of gpg may be extended utilizing partial nucleotide sequence and various methods known in the art to detect upstream sequences such as promoters and regulatory elements. Gobinda et al (1993; PCR Methods Applic 2:318–22) disclose "restriction-site polymerase chain reaction (PCR)" as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al(1988) Nucleic Acids Res 16:8186). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al (1991) PCR Methods Applic 1:111–19) is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR.

Parker J. D. et al (1991; Nucleic Acids Res 19:3055–60), teach walking PCR, a method for targeted gene walking which permits retrieval of unknown sequence. Promoter-Finder™ a new kit available from Clontech (Palo Alto Calif.) uses PCR, nested primers and PromoterFinder libraries to walk in genomic DNA. This process avoids the need to screen libraries and is useful in finding intron/exon junctions.

Another PCR method, "*Improved Method for Obtaining Full Length cDNA Sequences*" by Guegler et al, patent application Ser. No. 08/487,112, filed Jun. 7, 1995 and hereby incorporated by reference, employs XL-PCR™ (Perkin-Elmer) to amplify and/or extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension 5' of the promoter binding region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851–8).

Expression of the Nucleotide Sequence

In accordance with the present invention, gpg polynucleotide sequences which encode GPG, fragments of the polypeptide, fusion proteins or functional equivalents thereof, may be used to generate recombinant DNA molecules that direct the expression of GPG in appropriate host cells. Due to the inherent degeneracy of the genetic code, other DNA sequences which encode substantially the same or a functionally equivalent amino acid sequence, may be used to clone and express GPG. As will be understood by those of skill in the art, it may be advantageous to produce GPG-encoding nucleotide sequences possessing non-naturally occurring codons. Codons preferred by a particular prokaryotic or eukaryotic host (Murray E. et al (1989) Nuc Acids Res 17:477–508) can be selected, for example, to increase the rate of GPG expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of FIG. 1 under conditions of intermediate to maximal stringency. Hybridization conditions are based on the melting temperature (Tm) of the nucleic acid binding complex, as taught in Berger and Kimmel (1987, *Guide to Molecular Cloning Techniques, Methods in Enzymology*, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency"at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences. The term "hybridization" as used herein shall include "the process by which a strand of nucleic acid joins with a complementary strand through base pairing" (Coombs J. (1994) *Dictionary of Biotechnology*, Stockton Press, New York N.Y.) as well as the process of amplification as carried out in polymerase chain reaction technologies as described in Dieffenbach C. W. and G. S. Dveksler (1995, *PCR Primer, a Laboratory Manual*, Cold Spring Harbor Press, Plainview N.Y.) and incorporated herein by reference.

As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring gpg.

As used herein "substitution" results from the replacement of one or more nucleotides or amino acids by different nucleotides or amino acids, respectively.

Altered gpg polynucleotide sequences which may be used in accordance with the invention include deletions, insertions or substitutions of different nucleotide residues resulting in a polynucleotide that encodes the same or a functionally equivalent GPG. The protein may also show deletions, insertions or substitutions of amino acid residues which produce a silent change and result in a functionally equivalent GPG. Deliberate amino acid substitutions may be made on the basis of similarity in polarity, charge, solubility, hydrophobicity, hydrophilicity, and/or the amphipathic nature of the residues as long as the biological activity of GPG is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of gpg. As used herein, an "allele" or "allelic sequence" is an alternative form of gpg. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a gpg coding sequence for a variety of reasons, including but not limited to, alterations which modify the cloning, processing and/or expression of the gene product. For example, mutations may be introduced using techniques which are well known in the art, eg. site-directed mutagenesis to insert new restriction sites, to alter glycosylation patterns, to change codon preference, etc.

In another embodiment of the invention, a gpg natural, modified or recombinant sequence may be ligated to a heterologous sequence to encode a fusion protein. For example, for screening of peptide libraries for inhibitors of GPG activity, it may be useful to encode a chimeric GPG protein expressing a heterologous epitope that is recognized by a commercially available antibody. A fusion protein may also be engineered to contain a cleavage site located between a gpg sequence and the heterologous protein sequence, so that the GPG may be cleaved and purified away from the heterologous moiety.

In an alternate embodiment of the invention, the coding sequence of gpg could be synthesized, whole or in part, using chemical methods well known in the art (see Caruthers M. H. et al (1980) Nuc Acids Res Symp Ser 215–23. Horn T. et al(1980) Nuc Acids Res Symp Ser 225–32, etc). Alternatively, the protein itself could be produced using chemical methods to synthesize a gpg amino acid sequence, whole or in part. For example, peptides can be synthesized by solid phase techniques, cleaved from the resin, and purified by preparative high performance liquid chromatography (eg. Creighton (1983) Proteins Structures And Molecular Principles, W. H. Freeman and Co. New York N.Y.). The composition of the synthetic peptides may be confirmed by amino acid analysis or sequencing (eg. the Edman degradation procedure; Creighton, supra)

Direct peptide synthesis can be performed using various solid-phase techniques (Roberge J. Y. et al (1995) Science 269:202–204) and automated synthesis may be achieved, for example, using the ABI 431A Peptide Synthesizer (Perkin Elmer) in accordance with the instructions provided by the manufacturer. Additionally the amino acid sequence of GPG, or any part thereof, may be altered during direct synthesis and/or combined using chemical methods with sequence from other γ subunits, or any part thereof, to produce a variant polypeptide.

Expression Systems

In order to express a biologically active GPG, the nucleotide sequence coding for GPG, or a functional equivalent, is inserted into an appropriate expression vector, ie, a vector which contains the necessary elements for the transcription and translation of the inserted coding sequence.

Methods which are well known to those skilled in the art can be used to construct expression vectors containing a gpg coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual*, Cold Spring Harbor Press, Plainview N.Y. and Ausubel F. M. et al. (1989) *Current Protocols in Molecular Biology*, John Wiley & Sons, New York N.Y.

A variety of expression vector/host systems may be utilized to contain and express a gpg coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of gpg, vectors based on SV40 or EBV may be used with an appropriate selectable marker.

In bacterial systems, a number of expression vectors may be selected depending upon the use intended for GPG. For example, when large quantities of GPG are needed for the induction of antibodies, vectors which direct high level expression of fusion proteins that are readily purified may be desirable. Such vectors include, but are not limited to, the *E. coli* cloning and expression vector Bluescript® (Stratagene), in which the gpg coding sequence may be ligated into the vector in frame with sequences for the amino-terminal Met and the subsequent 7 residues of β-galactosidase so that a hybrid protein is produced; pIN vectors (Van Heeke G. & S. M. Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For a review of the vectors and promoters, see Ausubel et al (supra).

In cases where plant expression vectors are used, the expression of a gpg coding sequence may be driven by any of a number of promoters. For example, viral promoters such as the 35S or 19S promoters of CaMV (Rhodes C. A. et al (1988) Science 240:204–207) may be used alone or in combination with the omega leader sequence from TMV (Takamatsu N. et al (1987) EMBO J 6:307–311). Alternatively, plant promoters such as the small subunit of RUBISCO (Coruzzi G. et al (1984) EMBO J 3:1671–79; Broglie R. et al (1984) Science 224:838–43); or heat shock promoters (Winter J. and Sinibaldi R. M. (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Yearbook of Science and Technology (1992) McGraw Hill New York N.Y., pp 191–196.

An alternative expression system which could be used to express gpg is an insect system. In one such system, *Autographa californica* nuclear polyhedrosis virus (AcNPV) is used as a vector to express foreign genes in *Spodoptera frugiperda* cells or in *Trichoplusia larvae*. The gpg coding sequence may be cloned into a nonessential region of the virus, such as the polyhedrin gene, and placed under control of the polyhedrin promoter. Successful insertion of gpg will render the polyhedrin gene inactive and produce recombinant virus lacking coat protein coat. The recombinant viruses are then used to infect *S. frugiperda* cells or *Trichoplusia larvae* in which GPG is expressed (Smith G. et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, a gpg coding sequence may be ligated into an adenovirus transcription/translation complex consisting of the late promoter and tripartite leader sequence. Insertion in a nonessential E1 or E3 region of the viral genome will result in a viable virus capable of expressing GPG in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of an inserted gpg sequence. These signals include the ATG initiation codon and adjacent sequences. In cases where gpg, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D. et al (1994) Results Probl Cell Differ 20:125–62; Bittner M. et al (1987) Methods in Enzymol 1 53:51 6–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express GPG may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M. et al (1977) Cell 11:223–32) and adenine phosphoribosyltransferase (Lowy L et al (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler M. et al (1980) Proc Natl Acad Sci 77:3567–70); npt, which confers resistance to the aminoglycosides neomycin and G-418 (Colbere-Garapin F. et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C. A. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the gpg is inserted within a marker gene sequence, recombinant cells containing gpg can be identified by the absence of marker gene function. Alternatively, a marker gene can be placed in tandem with a gpg sequence under the control of a single promoter. Expression of the marker gene in response to induction or selection usually indicates expression of gpg as well.

Alternatively, host cells which contain the coding sequence for gpg and express GPG may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the gpg polynucleotide sequence can be detected by DNA-DNA or DNA-RNA hybridization or amplification using probes, portions or fragments of gpg. Nucleic acid amplification based assays involve the use of oligonucleotides or oligomers based on the gpg sequence to detect transformants containing gpg DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

The role of GPG in the mobilization of $Ca^{++}$ as part of the signal transduction pathway can be assayed in vitro. It requires preloading neutrophils or T cells with a fluorescent dye such as FURA-2 or BCECF (Universal Imaging Corp, Westchester Pa.) whose emission characteristics have been altered by $Ca^{++}$ binding. When the cells are exposed to one or more activating stimuli artificially (ie, anti-CD3 antibody ligation of the T cell receptor) or physiologically (ie, by allogeneic stimulation), $Ca^{++}$ flux takes place. This flux can be observed and quantified by assaying the cells in a fluorometer or fluorescent activated cell sorter. The measurement of $Ca^{++}$ mobilization in neutrophils has been described in Grynkievicz G. et al (1985) J Biol Chem 260:3440, and McColl S. et al (1993) J Immunol 150:4550–4555, and in T cells, in Aussel C. et al. (supra), incorporated herein by reference.

A variety of protocols for detecting and measuring the expression of GPG, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on GPG is preferred, but a competitive binding assay may be employed. These and other assays are described, among other places, in Hampton R. et al (1990, *Serological Methods, a Laboratory Manual*, APS Press, St Paul Minn.) and Maddox D. E. et al (1983, J Exp Med 158:1211).

A wide variety of labels and conjugation techniques are known by those skilled in the art and can be used in various nucleic and amino acid assays. Means for producing labelled hybridization or PCR probes for detecting sequences related to gpg include oligolabelling, nick translation, end-labelling or PCR amplification using a labelled nucleotide. Alternatively, the gpg sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of GPG

Host cells transformed with a gpg nucleotide sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing gpg can be designed with signal sequences which direct secretion of GPG through a particular prokaryotic or eukaryotic cell membrane. Other recombinant constructions may join gpg to nucleotide sequence encoding a polypeptide domain which will facilitate purification of soluble proteins (Kroll D. J. et al (1993) DNA Cell Biol 12:441–53; see also above discussion of vectors containing fusion proteins).

GPG may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash). The inclusion of a cleavable linker sequences such as Factor XA or enterokinase (Invitrogen, San Diego Calif.) between the purification domain and GPG is useful to facilitate purification.

Uses of GPG

The rationale for diagnostic and therapeutic uses of GPG sequences is based on the nucleotide and amino acid sequences, their homology to the rat G protein γ subunit, their tissue distribution in uterus, neonatal keratinocytes, T cells, neutrophils, and stimulated macrophages, and the known associations and functions of heterotrimeric and dimeric G proteins. The nucleic acid sequence presented in FIG. 1, its complement, fragments or oligomers, and anti-GPG antibodies may be used as diagnostic compositions in assays of cells, tissues or their extracts. Purified gpg or GPG can be used as the positive controls in their respective nucleic acid or protein based assays for conditions or diseases characterized by the excess expression of GPG. Antisense molecules, antagonists or inhibitors capable of specifically binding gpg or GPG can be used as pharmaceutical compositions for conditions or diseases characterized by the excess expression of GPG. Such conditions include activation of leukocytes and lymphocytes in autoimmune diseases and cell proliferation associated with endometriosis or tumor formation.

The regulation of γ subunit expression or of dimer formation and activity provides an opportunity for early intervention in conditions based on cell proliferation. In endometriosis, menstrual tissue is found outside the uterus (in the fallopian tubes, around the ovaries and in the abdomen). These endometrial cells as well as those located in the uterus respond to the monthly hormone cycle by swelling and bleeding. This condition, which can be quite painful, is seen in 10–15% of women between 25 and 44 and shows a familial inheritance pattern (The Merck Manual of Diagnosis and Therapy (1992) Merck Research Laboratories, Rahway N.J.). Since estrogen is the stimulus for the cell cycle cascades which result in endometrial proliferation, pharmaceutical intervention in this condition has been based on suppressing estrogen.

In less severe cases of endometriosis, especially in women beyond their child bearing years, contraceptives are the prescribed therapy. In more recalcitrant cases, administration of Danocrine® (Sanofi Winthrop, New York N.Y.) which suppresses the pituitary-ovarian axis has been more successful, but has caused virilizing side effects in some women. Although surgery cannot guarantee the removal of all endometrial cells, it has provided temporary relief for women with extreme abdominal proliferation and pain.

For extra-uterine endometriosis, a vector containing and capable of expressing gpg antisense sequences, peptide nucleic acids (PNA), or inhibitors of GPG can be introduced in liposomes via abdominal lavage, particularly after surgery. Suppression of estrogen induced signal can prevent endometrial proliferation while not interfering with the regular uterine menstrual cycle. This treatment would be particularly effective following surgical removal of endometrial tissue form the abdomen.

In an analogous manner, appropriate delivery of vectors expressing antisense sequences, peptide nucleic acids (PNA), or inhibitors of GPG can be used to prevent cell proliferation producing tumors in endocrine hormone-stimulated tissues such as the pituitary gland, thyroid, adrenal glands, testes or ovaries. Delivery of these therapies, further described below under Pharmaceutical Compositions, is necessarily tissue/tumor specific and depend on the diagnosis, size and status of neoplasm or tumor.

The regulation of γ subunit expression or of dimer formation and activity provides an opportunity to intervene in the activation of leukocytes and lymphocytes. Activation of T cells requires at least two signals, one cell surface, for example, the T cell receptor, and one soluble, for example, IL-2. The soluble factors are secreted by accessory cells and interact with specific receptors on the surface of T cells. Specific examples of T cell activation as a G protein regulated process are presented in Aussel C. et al. (supra).

Inappropriate activation of leukocytes or lymphocytes may result in the tissue damage and destruction seen in autoimmune diseases such as rheumatoid arthritis, biliary cirrhosis, hemolytic anemia, lupus erythematosus, and thyroiditis. For example, transfection of the leukocytes or lymphocytes of the rheumatoid synovium with vectors expressing antisense sequences or with liposomes bearing PNAs or inhibitors of GPG can be used to avoid the formation of functional G protein dimers and subsequent activation of the leukocytes and lymphocytes which perpetuate tissue destruction.

GPG Antibodies

Procedures well known in the art can be used for the production of antibodies to GPG Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc may be immunized by injection with GPG or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to GPG may be prepared using any technique which provides for the production of antibody molecules by continuous cell lines in culture. These include but are not limited to the hybridoma technique originally described by Koehler and Milstein (1975 Nature 25 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R. Liss Inc, New York N.Y., pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce GPG-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C. (1991; Nature 349:293–299).

Antibody fragments which contain specific binding sites for GPG may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W. D. et al (1989) Science 256:1275–1281).

GPG-specific antibodies are useful for the diagnosis of conditions and diseases associated with excessive expression of GPG. A variety of protocols for competitive binding or immunoradiometric assays using either polyclonal or monoclonal antibodies with established specificities are well known in the art. Such immunoassays typically involve the formation of complexes between GPG and its specific antibody and the measurement of complex formation. A two-site, monoclonal-based immunoassay utilizing monoclonal antibodies reactive to two noninterfering epitopes on a specific GPG protein is preferred, but a competitive binding assay may also be employed. These assays are described in Maddox D. E. et al (1983, J Exp Med 158:1211).

Diagnostic Assays Using GPG Specific Antibodies

Particular GPG antibodies are useful for the diagnosis of conditions or diseases characterized by excessive expression of GPG. Diagnostic assays for GPG include methods utilizing the antibody and a label to detect GPG in human body fluids, cells, tissues or extracts of such tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring GPG, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on GPG is preferred, but a competitive binding assay may be employed. These assays are described, among other places, in Maddox, D. E. et al (1983, J Exp Med 158:1211).

In order to provide a basis for the diagnosis of disease, normal or standard values for GPG expression must be established. This is accomplished by combining body fluids or cell extracts taken from normal subjects, either animal or human, with antibody to GPG under conditions suitable for complex formation which are well known in the art. The amount of standard complex formation may be quantified by comparing it with a dilution series of positive controls where a known amount of antibody is combined with known concentrations of purified GPG. Then, standard values obtained from normal samples may be compared with values obtained from samples from subjects potentially affected by a disorder or disease related to GPG expression. Deviation between standard and subject values establishes the presence of disease state.

Drug Screening

GPG, its catalytic or immunogenic fragments or oligopeptides can be used for screening therapeutic compounds in any of a variety of drug screening techniques. The fragment employed in such a test may be free in solution, affixed to a solid support, borne on a cell surface, or located intracellularly. The abolition of catalytic activity or the formation of binding complexes, between GPG and the agent being tested, may be measured.

Another technique for drug screening which provides for high throughput screening of compounds having suitable binding affinity to the GPG is described in detail in "Determination of Amino Acid Sequence Antigenicity" by Geysen HN, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of GPG and washed. Bound GPG is then detected by methods well known in the art. Purified GPG can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding GPG specifically compete with a test compound for binding GPG. In this manner, the antibodies can be used to detect the presence of any peptide which shares one or more antigenic determinants with GPG.

Uses of the Polynucleotide Encoding GPG

A polynucleotide, gpg, or any part thereof, may be used for diagnostic and/or therapeutic purposes. For diagnostic purposes, the gpg of this invention may be used to detect and quantitate gene expression in conditions or diseases in which GPG activity may be implicated. These specifically include, but are not limited to, activation of leukocytes and lymphocytes in autoimmune diseases, and cell proliferation in endometriosis and tumors, particularly of tissues with endocrine functions. Included in the scope of the invention are oligonucleotide sequences, antisense RNA and DNA molecules, PNAs and ribozymes, which function to inhibit translation of a GPG.

Another aspect of the subject invention is to provide for hybridization or PCR probes which are capable of detecting polynucleotide sequences, including genomic sequences, encoding GPG or closely related molecules. The specificity of the probe, whether it is made from a highly conserved region, eg, 10 unique nucleotides in the 5' regulatory region, or a less conserved region, eg, between cysteine residues especially in the 3' region, and the stringency of the hybridization or amplification (high, intermediate or low) will determine whether the probe identifies only naturally occurring GPG or related sequences.

Diagnostics

Polynucleotide sequences encoding GPG may be used for the diagnosis of diseases resulting from excessive expression of gpg. For example, polynucleotide sequences encoding GPG may be used in hybridization or PCR assays of tissues from biopsies or autopsies to detect abnormalities in gpg expression. The form of such qualitative or quantitative methods may include Southern or northern analysis, dot blot or other membrane-based technologies; PCR technologies; dip stick, pin, chip and ELISA technologies. All of these techniques are well known in the art, and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for gpg expression must be established. This is accomplished by combining body fluids or cell extracts taken from normal subjects, either animal or human, with gpg or a portion thereof, under conditions suitable for hybridization or amplification. Standard hybridization may be quantified by comparing the values obtained for normal subjects with a dilution series of positive controls run in the same experiment where a known amount of purified gpg is used. Standard values obtained from normal samples may be compared with values obtained from samples from subjects potentially affected by a disorder or disease related to gpg expression. Deviation between standard and subject values establishes the presence of the disease state.

If disease is established, an existing therapeutic agent is administered, and a treatment profile may be generated. Finally, the assay may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195; 4,800,195; and 4,965,188 provides additional uses for oligonucleotides based upon the gpg sequence. Such oligomers are generally chemically synthesized, but they may be generated enzymatically or produced from a recombinant source. Oligomers generally comprise two nucleotide sequences, one with sense orientation (5'→3') and one with antisense (3'→5') employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally methods to quantitate the expression of a particular molecule include radiolabeling (Melby P. C. et al 1993 J Immunol Methods 159:235–44) or biotinylating (Duplaa C. et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer-of-interest is presented in various dilutions and a spectrophotometric or colorimetric response gives rapid quantitation. For example, increased gpg in fluid removed from a rheumatoid synovium may indicate leukocyte and lymphocyte activation and progressive tissue destruction. A definitive diagnosis of this type may allow health professionals to treat the patient and prevent further worsening of the condition. Similarly, assays known to those of skill in the art can be used to monitor the progress of a patient displaying a gpg associated disease state during therapy.

Therapeutics

An antisense sequence based on the gpg sequence of this application may be useful in the treatment of various conditions or diseases. By introducing antisense sequence into cells, gene therapy can be used to treat conditions or diseases characterized by overexpression of GPG. In such instances, the antisense sequence binds with the complementary DNA strand and either prevents transcription or stops transcript elongation (Hardman J. G. et al. (1996) *Goodman and Gilson's The Pharmacological Basis of Therapeutics*. McGraw Hill, New York N.Y.)

Expression vectors derived retroviruses, adenovirus, herpes or vaccinia viruses, or from various bacterial plasmids, may be used for delivery of antisense sequences to the targeted cell population. Methods which are well known to those skilled in the art can be used to construct recombinant vectors which will express the antisense sequence. See, for example, the techniques described in Maniatis et al (supra) and Ausubel et al (supra). Alternatively, antisense molecules such as PNAs can be produced and delivered to target cells or tissues in liposomes.

The full length cDNA sequence and/or its regulatory elements enable researchers to use gpg as a tool in sense (Youssoufian H. and H. F. Lodish 1993 Mol Cell Biol 13:98–104) or antisense (Eguchi et al (1991) Annu Rev Biochem 60:631–652) investigations or regulation of gene function. Such technology is now well known in the art, and sense or antisense oligomers, or larger fragments, can be designed from various locations along the coding or control regions.

Sequences encoding GPG can be turned off by transfecting a cell or tissue with expression vectors which express high levels of a gpg fragment. Such constructs can flood cells with untranslatable sense or antisense sequences. Even in the absence of integration into the DNA, such vectors may continue to transcribe RNA molecules until all copies are disabled by endogenous nucleases. Such transient expression may last for a month or more with a non-replicating vector (Mettler I, personal communication) and even longer if appropriate replication elements are part of the vector system.

On the other hand, stable transformation of appropriate germ line cells, or preferably a zygote, with a vector containing gpg fragments may produce a transgenic organism (U.S. Pat. No. 4,736,866, 12 Apr. 1988), which produces enough copies of the sense or antisense sequence to significantly compromise or entirely eliminate activity of the naturally occurring gpg gene.

As mentioned above, modifications of gene expression can be obtained by designing antisense DNA or RNA molecules or PNAs to the control regions of gpg, ie. the promoters, enhancers, and introns. Oligonucleotides derived from the transcription initiation site, eg. between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al. (In Huber B. E. and B. I. Carr (1994) *Molecular and Immunologic Approaches*. Futura Publ. Co, Mt Kisco N.Y.).

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of gpg.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding GPG. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. Ex vivo therapy, the introduction of vectors into stem cells taken from the patient and clonally propagated for autologous transplant back into that same patient is presented in U.S. Pat. Nos. 5,399,493 and 5,437,994, disclosed herein by reference.

Furthermore, the nucleotide sequences for gpg disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for gpg can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as YACs, bacterial artificial chromosomes (BACs), bacterial P1 constructions or single chromosome cDNA libraries (reviewed in Price C. M. (1993) Blood Rev 7:127–34 and Trask B. J. (1991) Trends Genet 7:149–54).

In situ hybridization of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal, carrier or affected individuals.

Pharmaceutical Compositions

The present invention comprises pharmaceutical compositions which may comprise antibodies, antagonists, or inhibitors of GPG, alone or in combination with at least one other agent, such as stabilizing compound, which may be administered in any sterile, biocompatible pharmaceutical carrier, including, but not limited to, saline, buffered saline, dextrose, and water.

Antagonists, or inhibitors of GPG can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert. Since GPG is a cytoplasmic subunit which associates with other subunits in order to carry out cell signaling, the preferred route for administration these antagonists or inhibitors by vesicular including liposome technology.

Antagonists or inhibitors of GPG may be used alone or in combination with other chemotherapeutic molecules to prevent activation of leukocytes and lymphocytes or cell proliferation associated with endometriosus or growth and development of tumors of endocrine tissues. For example, liposomes carrying antagonists or inhibitors may be injected into inflamed rheumatoid synovia. The fusion of these liposomes with leukocytes or lymphocytes in the synovium compromises the activation process and reduces inflammation. In the case of Antagonists and inhibitors destined for endocrine tissue are administered locally in vesicles targeted to the tissue of interest.

An effective amount of GPG inhibitor, alone or in combination with antisense molecules, may be administered in liposomes via abdominal lavage to females with endometriosis. The treatment parallels the antibiotic lavage administered in cases of burst appendix and may be repeated for two to three months to eliminate all endometrial cells. This lavage of therapeutic nucleotide and ligand molecules would work by inhibiting dimer and heterotrimer formation and by suppressing gpg expression.

Further details on techniques for formulation and administration may be found in the latest edition of "Remington's Pharmaceutical Sciences" (Mack Publishing Co, Easton Pa.). Although local delivery is desirable, there are other means, for example, oral; parenteral delivery, including intra-arterial (directly to the tumor), intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art.

The pharmaceutical compositions can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. The determination of an effective dose is well within the capability of those skilled in the art, especially in light of the disclosure provided below.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, eg, by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For administration of GPG, such labeling would include amount, frequency and method of administration.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays, eg, of neoplastic cells. Then, preferably, dosage can be formulated in animal models affected with the neoplasm to achieve a desirable concentration range and route of administration that inhibits MMPs. Such information can be used to determine useful doses and route of administration in humans.

A therapeutically effective dose refers to that amount of antisense molecules or inhibitors of GPG which ameliorates symptoms, eg, prevents cell proliferation. Toxicity and therapeutic efficacy of such compounds can be determined by standard pharmaceutical procedures in cell cultures or experimental animals, eg. for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds, GPG variants or fragments, which exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg. tumor size and location; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. No. 4,657,760; 5,206,344; or 5,225,212. Those skilled in the art will employ different formulations for antisense molecules than for the inhibitors of GPG. Similarly, administration of gpg to a T cell will necessitate delivery in a manner different from that of a GPG inhibitor being delivered to endometrial cells.

It is contemplated that conditions associated with known activities of GPG are treatable with either antisense or PNA molecules of gpg or antagonists or inhibitors of GPG. The timing of and amount of expression of GPG is implicated in activation of leukocytes or lymphocytes in autoimmune diseases such as rheumatoid arthritis, biliary cirrhosis, hemolytic anemia, lupus erythematosus, and thyroiditis and in cell proliferation associated with endometriosis or with the formation of tumors of brain, thyroid, adrenal, and gonadal tissues. The assays previously discussed may be used to diagnose or treat these conditions and to monitor such treatment.

The examples below are provided to illustrate the subject invention. These examples are provided by way of illustration and are not included for the purpose of limiting the invention.

EXAMPLES

I Pituitary cDNA Library Construction

The human pituitary library was constructed from a pooled sample of 21 whole, pituitary glands from brains of Caucasian males and females with a range of ages from 16–70 years. The poly A+ RNA was obtained from Clontech Laboratories Inc. (Catalogue #6584-1 and #6584-2, Palo Alto Calif.), and Stratagene (La Jolla Calif.) used the poly A+ RNA to construct the library. cDNA synthesis was primed using both oligo d(T) and random hexamers, and the two cDNA libraries were handled separately. Synthetic adapter oligonucleotides were ligated onto the ends of the cDNA molecules enabling insertion into the Stratagene Uni-ZAP™ vector system. Phagemid forms of individual cDNA clones were obtained by the in vivo excision process, in which the host bacterial strain, XL1-Blue® (Stratagene), was co-infected with both the library phage and an f1 helper phage. Equal numbers of bacteriophage from the two cDNA libraries were mixed and used to reinfect fresh host cells (SOLR, Stratagene) where double-stranded phagemid DNA was produced. The newly transformed bacteria were selected on medium containing ampicillin.

II Isolation and Sequencing of cDNA Clones

Phagemid DNA was purified using the QIAWELL-8 Plasmid Purification System (QIAGEN Inc, Chatsworth Calif.) including the recommended protocols and prepared for sequencing. The cDNA inserts from random isolates of the pituitary library were sequenced by the method of Sanger F. and A. R. Coulson (1975; J Mol Biol 94:441f). Methods for DNA sequencing are well known in the art and use DNA polymerase Klenow fragment, SEQUENASE™ (US Biochemical Corp, Cleveland Ohio) or Taq polymerase to extend DNA chains from an oligonucleotide primer annealed to the DNA template of interest. Methods have been developed to sequence both single- and double-stranded templates.

The chain termination reaction products were electrophoresed on urea-polyacrylamide gels and detected by fluorescence. The pituitary cDNAs were prepared and sequenced using the ABI Catalyst 800 and 377 or 373 DNA sequencers (Perkin Elmer, Norwalk Conn.).

III Homology Searching of CDNA Clones and Their Deduced Proteins

Each cDNA was compared to sequences in GenBank using a search algorithm incorporated into the INHERIT™ Sequence Analysis System (Perkin Elmer). In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Extension of the Polynucleotide Sequence to Recover Regulatory Elements

The nucleic acid sequence of full length gpg (SEQ ID NO:1) or any of the related or variant molecules (SEQ ID NOs: 9–31) may be used to design oligonucleotide primers for obtaining control sequences from genomic libraries. One primer is synthesized to initiate extension in the antisense direction (XLR) and the other is synthesized to extend sequence in the sense direction (XLF). The primers allowed the known gpg sequence to be extended "outward" generating amplicons containing new, unknown nucleotide sequence for the control region of interest. The initial primers may be designed from the cDNA using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

A human genomic library is used to extend and amplify 5' upstream sequence. If necessary, a second set of primers is designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J. et al. supra). After incubation for one hour at 37° C., the whole transformation mixture is plated on Luria Bertani (LB)-agar (Sambrook J. et al, supra) containing 2× Carb. The following day, several colonies are randomly picked from each plate and cultured in 150 µl of liquid LB/2× carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO:1 may be employed to screen cDNAs, mRNAs or genomic DNAs. Although the labeling of oligonucleotides, consisting of about 20 base-pairs, is specifically described, essentially the same procedure may be used with larger cDNA fragments. Oligonucleotides are labeled by combining 50 pmol of each oligomer and 250 mCi of [$\gamma$-$^{32}$P] adenosine triphosphate (Amersham, Chicago Ill.) and T4 polynucleotide kinase (DuPont NEN® Boston Mass.). The labeled oligonucleotides are purified with Sephadex G-25 super fine resin column (Pharmacia). A portion containing $10^7$ counts per minute of each is used in a typical membrane based hybridization analysis of human genomic DNA digested with one of the following endonucleases (Ase I, Bgl II, EcoR I, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The gpg sequence, or any part thereof, provides the basis for the design of antisense molecules which may be used to inhibit in vivo expression of naturally occurring gpg (see Hardman J. G. et al. supra) Although use of antisense oligomers, consisting of approximately 20 base-pairs, is specifically described, essentially the same procedure may be used with larger or smaller nucleic acid fragments. A complementary oligonucleotide based on the 5' untranslated region of gpg may be used to inhibit expression of naturally occurring gpg. The complementary oligonucleotide can be designed to inhibit transcription by preventing promoter binding or translation of a gpg transcript by preventing the ribosomal binding.

VII Expression of GPG

Expression of the GPG may be accomplished by subcloning the cDNAs into appropriate vectors and transfecting the vectors into host cells. The vector, pBluescript, is used to express GPG in *E. coli*, strain XL1-BlueMRF™ (Stratagene). Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length gpg. A signal sequence may be added to direct the secretion of GPG into the bacterial growth media for easier purification.

VIII GPG Activity

GPG can readily be assayed in vitro by monitoring the mobilization of $Ca^{++}$ in neutrophil signal transduction pathways. Neutrophils are preloaded with purified GPG and with a fluorescent dye such as FURA-2 or BCECF (Universal Imaging Corp) whose emission characteristics have been altered by $Ca^{++}$ binding. Then, the cells are exposed to allogeneic stimulation and $Ca^{++}$ flux is observed and quantified using a fluorescent activated cell sorter. Measurements of $CA^{++}$ flux are compared between cells in their normal state and those preloaded with GPG. Increased mobilization attributable to increased GPG availability results in increased emission.

IX Production of GPG Specific Antibodies

Although GPG purified using PAGE electrophoresis (Maniatis, supra) can be used to immunize rabbits using standard protocols, a monoclonal approach is more easily employed. The amino acid sequence translated from GPG is analyzed using DNASTAR software (DNASTAR Inc) to determine regions of high immunogenicity and a corresponding oligopeptide is synthesized and used to raise antibodies by means known to those of skill in the art. Analysis to select appropriate epitopes, such as those near the C-terminus or in adjacent hydrophilic regions is described by Ausubel F. M. et al (supra).

Typically, the oligopeptides are 15 residues in length, synthesized using an ABI Peptide Synthesizer Model 431A (Perkin Elmer) using fmoc-chemistry, and coupled to keyhole limpet hemocyanin (KLH, Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

X Purification of Naturally occurring GPG Using Specific Antibodies

Naturally occurring or recombinant GPG can be purified by immunoaffinity chromatography using antibodies specific for GPG. An immunoaffinity column is constructed by covalently coupling GPG antibody to an activated chromatographic resin such as CnBr-activated Sepharose (Pharmacia Biotech). After the coupling, the resin is blocked and washed according to the manufacturer's instructions.

Media containing GPG is passed over the immunoaffinity column, and the column is washed under conditions that allow the preferential absorbance of GPG (eg, high ionic strength buffers in the presence of detergent). The column is eluted under conditions that disrupt antibody/GPG binding (eg, a buffer of pH 2–3 or a high concentration of a chaotrope such as urea or thiocyanate ion), and GPG is collected.

XI Identification of Molecules Which Interact with GPG

GPG, or biologically active fragments thereof, is labeled with $^{125}I$ Bolton-Hunter reagent (Bolton, A. E. and Hunter, W. M. (1973) Biochem J 133: 529). Candidate molecules previously arrayed in the wells of a 96 well plate are incubated with the labeled GPG, washed and any wells with labeled GPG complex are assayed. Data obtained using different concentrations of GPG are used to calculate values for the number, affinity, and association of GPG with the candidate inhibitory molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A purified polynucleotide consisting of the sequence of SEQ ID NO:1, or its complement.

2. An expression vector comprising the polynucleotide sequence of claim 1.

3. A host cell transformed with the expression vector of claim 2.

4. A method for producing a polypeptide comprising the amino acid sequence shown in SEQ ID NO:2, the method comprising the steps of:
    (a) culturing the host cell of claim 3 to allow expression of the polypeptide; and
    (b) recovering the polypeptide from the host cell culture.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear (ii) MOLECULE TYPE: cDNA (vii) IMMEDIATE SOURCE:
(A) LIBRARY: PITUITARY
(B) CLONE: 112530

(xi) SEQUENCE DESCRIPTION: SEQ ID NO:1:

| | | | | | | |
|---|---|---|---|---|---|---|
| AAAGTTCGGA | GCCCTGCCCC | NGCCGCGCGC | CGCTGAGTTG | TCTGGCCCCG | CCGACCCACG | 60 |
| GCCCACGACC | CACCGACCCA | CGAATCGGCC | CGGCCGTCGC | GTGCACCATG | TCTGGCTCCT | 120 |
| CCAGCGTCGC | CGCTATGAAG | AAAGTGGTTC | AACAGCTCCG | GCTGGAGGCC | GGACTCAACC | 180 |
| GCGTAAAAGT | TTCCCAGGCA | GCTGCAGACT | TGAAACAGTT | CTGTCTGCAG | AATGCTCAAC | 240 |
| ATGACCCTCT | GCTGACTGGA | GTATCTTCAA | GTACAAATCC | CTTCAGACCC | CAGAAAGTCT | 300 |
| GTTCCTTTTT | GTAGTAAAAT | GAATCTTTCA | AAGGTTTCCC | AAACCACTCC | TTATGATCCA | 360 |
| GTGAATATTC | AAGAGGAGCT | ACATTTGAAG | CCT | | | 393 |

(2) INFORMATION FOR SEQ ID NO:2:

(i) SEQUENCE CHARACTERISTICS:
(A) LENGTH: 68 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: PITUITARY
(B) CLONE: 112530

(xi) SEQUENCE DESCRIPTION: SEQ ID NO:2:

| Met | Ser | Gly | Ser | Ser | Ser | Val | Ala | Ala | Met | Lys | Lys | Val | Val | Gln | Gln |
|---|---|---|---|---|---|---|---|---|---|---|---|---|---|---|---|
| 1 | | | | 5 | | | | | 10 | | | | | 15 | |
| Leu | Arg | Leu | Glu | Ala | Gly | Leu | Asn | Arg | Val | Lys | Val | Ser | Gln | Ala | Ala |
| | | | 20 | | | | | 25 | | | | | 30 | | |
| Ala | Asp | Leu | Lys | Gln | Phe | Cys | Leu | Gln | Asn | Ala | Gln | His | Asp | Pro | Leu |
| | | | 35 | | | | 40 | | | | | 45 | | | |
| Leu | Thr | Gly | Val | Ser | Ser | Ser | Thr | Asn | Pro | Phe | Arg | Pro | Gln | Lys | Val |
| | | 50 | | | | 55 | | | | | 60 | | | | |
| Cys | Ser | Phe | Leu |
| 65 | | | |

(2) INFORMATION FOR SEQ ID NO:3:

(i) SEQUENCE CHARACTERISTICS:
(A) LENGTH: 1392 base pairs
(B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY: GenBank
(B) CLONE: 204241

(xi) SEQUENCE DESCRIPTION: SEQ ID NO:3:

| | | | | | | |
|---|---|---|---|---|---|---|
| AGTTGGCCCG | GCTGTCCGA | GCGCCATGTC | GGGTTCTTCT | AGCGTCGCCG | CCATGAAGAA | 60 |
| GGTGGTTCAG | CAACTCCGGC | TGGAGGCCGG | GCTCAACCGC | GTGAAGGTTT | CCCAGGCAGC | 120 |
| TGCAGACTTG | AAACAGTTCT | GTCTGCAGAA | TGCTCAACAT | GACCCTCTGC | TGACTGGAGT | 180 |
| GTCTTCAAGT | ACAAATCCCT | TCAGACCCCA | GAAAGTCTGC | TCCTTTTTGT | AGTCATATAT | 240 |

-continued

| | | | | | |
|---|---|---|---|---|---|
| CTCGAGGTTT | CTCAAACTAC | TTTTCATGAA | CCAGTGAATA | TTCACGAGAA | CTAAGTTCGA | 300 |
| AGTCACTAAG | TTTGAAGTCT | GTACAGAAGC | TTCTCTTTAA | CACGTGCCAT | ACACATAATC | 360 |
| TTCTACTCGT | CAGTCCTTAA | CATCTACCTC | TCTGGATTTT | CATGGATCTC | TGTTTCACAA | 420 |
| GGTTTAACTG | TTTTATATAC | ACTGGCTGTA | GCATACAATA | AAGCAGCATA | CAAACTTTTG | 480 |
| GCCTTGTTAT | TGATATGAAA | TGTGCTGTAT | ACTAATTTTT | TCAACATCAG | GACTCACTGC | 540 |
| CTTATTGGCA | AGGCTTCTAG | GAATTTACAG | AACAACTGCA | ATCTTTGTT | CAAAGGCCGG | 600 |
| AAGACTTAAG | AGTTTCTAAT | CCTTCAGTCA | GTTATGGGAA | TTATCTTAAA | TATCCCAAAT | 660 |
| ATAGGTAGGG | AGATGGCTCG | GTGGCTAAGA | GCACTTGCTC | TGCAGTTAGT | TATGCTGAGT | 720 |
| TCAGATCCTG | CCACCCATGT | AAAAAGCTGG | GCGTGGCTGT | ACATGCCCGT | GGCCACAGCT | 780 |
| TCGGGGAGAT | GGTTTGTTGG | CTGCCAGCGA | GGGTAAGGTT | GTAATTAGCT | CCGTGAGAAC | 840 |
| GAGGCAGAAA | GGGATACAGG | TGCCTGACAC | TGCCATGTGG | GCTCACACAG | GCAACAAACA | 900 |
| ACTCTAGTGG | CGTCAGCAGT | TAGTGCTACC | AAGAAGGTGG | CTGCTTCCAT | CTGGAAAAAG | 960 |
| AGTTAAAGAT | TCACAGAATC | AAGACCTTGA | GGACTTACGA | CAATGCCTCA | AGTAGGCAAG | 1020 |
| TGGAGGTAAT | TAGGTAGAAA | GGAACAAGAA | AACAGGTTAA | CCTCTGTGAC | CTGTAACTTT | 1080 |
| GCTCCAAGTC | CCAATAACCT | GTCCTTTAGA | ACTGGTATAT | TAAATCAGGG | TCATACACTA | 1140 |
| TCTACCAACA | AGCCTTTTTT | CTAGCCTACA | AGTTCTTTGG | GAATGAAAAT | TATAAAGTTT | 1200 |
| GAATCGTCAT | TCCTAAGAAA | TTATTACAAC | TAATCCAAAA | TGACAACAGC | TTTTATGACT | 1260 |
| TTCATACATA | ATTTTTCAGA | CAAAAATAAA | ATTATATTTA | TTTATATTTA | CTATATGCAG | 1320 |
| TGGAAACTCA | TAGCACTTGG | TCATTTCTTC | AAACACAGGA | TTTATAAAAT | AAAATCCCAT | 1380 |
| TTTGAAAAGT | AA | | | | | 1392 |

( 2 ) INFORMATION FOR SEQ ID NO:4:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 204241

( x i ) SEQUENCE DESCRIPTION: SEQ ID NO:4:

```
Met Ser Gly Ser Ser Ser Val Ala Ala Met Lys Lys Val Val Gln Gln
 1               5                  10                  15

Leu Arg Leu Glu Ala Gly Leu Asn Arg Val Lys Val Ser Gln Ala Ala
                20                  25                  30

Ala Asp Leu Lys Gln Phe Cys Leu Gln Asn Ala Gln His Asp Pro Leu
            35                  40                  45

Leu Thr Gly Val Ser Ser Ser Thr Asn Pro Phe Arg Pro Gln Lys Val
        50                  55                  60

Cys Ser Phe Leu
65
```

( 2 ) INFORMATION FOR SEQ ID NO:5:

( i ) SEQUENCE CHARACTERISTICS:
        ( A ) LENGTH: 74 amino acids
        ( B ) TYPE: amino acid
        ( C ) STRANDEDNESS: single
        ( D ) TOPOLOGY: linear (ii) MOLECULE TYPE: peptide (vii) IMMEDIATE SOURCE:
    (A) LIBRARY: GenBank
    (B) CLONE: 163787

(xi) SEQUENCE DESCRIPTION: SEQ ID NO:5:

| Met | Pro | Val | Ile | Asn | Ile | Glu | Asp | Leu | Thr | Glu | Lys | Asp | Lys | Leu | Lys |
|---|---|---|---|---|---|---|---|---|---|---|---|---|---|---|---|
| 1 | | | | 5 | | | | | 10 | | | | | 15 | |
| Met | Glu | Val | Asp | Gln | Leu | Lys | Lys | Glu | Val | Thr | Leu | Glu | Arg | Met | Leu |
| | | | 20 | | | | | 25 | | | | | 30 | | |
| Val | Ser | Lys | Cys | Cys | Glu | Glu | Phe | Arg | Asp | Tyr | Val | Glu | Glu | Arg | Ser |
| | | 35 | | | | | 40 | | | | | 45 | | | |
| Gly | Glu | Asp | Pro | Leu | Val | Lys | Gly | Ile | Pro | Glu | Asp | Lys | Asn | Pro | Phe |
| | 50 | | | | | 55 | | | | | 60 | | | | |
| Lys | Glu | Leu | Lys | Gly | Gly | Cys | Val | Ile | Ser | | | | | | |
| 65 | | | | | 70 | | | | | | | | | | |

(2) INFORMATION FOR SEQ ID NO:6:

(i) SEQUENCE CHARACTERISTICS:
    (A) LENGTH: 71 amino acids
    (B) TYPE: amino acid
    (C) STRANDEDNESS: single
    (D) TOPOLOGY: linear (ii) MOLECULE TYPE: peptide (vii) IMMEDIATE SOURCE:
    (A) LIBRARY: GenBank
    (B) CLONE: 163117

(xi) SEQUENCE DESCRIPTION: SEQ ID NO:6:

| Met | Ala | Ser | Asn | Asn | Thr | Ala | Ser | Ile | Ala | Gln | Ala | Arg | Lys | Leu | Val |
|---|---|---|---|---|---|---|---|---|---|---|---|---|---|---|---|
| 1 | | | | 5 | | | | | 10 | | | | | 15 | |
| Glu | Gln | Leu | Lys | Met | Glu | Ala | Asn | Ile | Asp | Arg | Ile | Lys | Val | Ser | Lys |
| | | | 20 | | | | | 25 | | | | | 30 | | |
| Ala | Ala | Ala | Asp | Leu | Met | Ala | Tyr | Cys | Glu | Ala | His | Ala | Lys | Glu | Asp |
| | | 35 | | | | | 40 | | | | | 45 | | | |
| Pro | Leu | Leu | Thr | Pro | Val | Pro | Ala | Ser | Glu | Asn | Pro | Phe | Arg | Glu | Lys |
| | 50 | | | | | 55 | | | | | 60 | | | | |
| Lys | Phe | Phe | Cys | Ala | Ile | Leu | | | | | | | | | |
| 65 | | | | | 70 | | | | | | | | | | |

(2) INFORMATION FOR SEQ ID NO:7:

(i) SEQUENCE CHARACTERISTICS:
    (A) LENGTH: 75 amino acids
    (B) TYPE: amino acid
    (C) STRANDEDNESS: single
    (D) TOPOLOGY: linear (ii) MOLECULE TYPE: peptide (vii) IMMEDIATE SOURCE:
    (A) LIBRARY: GenBank
    (B) CLONE: 163084

(xi) SEQUENCE DESCRIPTION: SEQ ID NO:7:

| Met | Lys | Gly | Glu | Thr | Pro | Val | Asn | Ser | Thr | Met | Ser | Ile | Gly | Gln | Ala |
|---|---|---|---|---|---|---|---|---|---|---|---|---|---|---|---|
| 1 | | | | 5 | | | | | 10 | | | | | 15 | |
| Arg | Lys | Met | Val | Glu | Gln | Leu | Lys | Ile | Glu | Ala | Ser | Leu | Cys | Arg | Ile |
| | | | 20 | | | | | 25 | | | | | 30 | | |
| Lys | Val | Ser | Lys | Ala | Ala | Ala | Asp | Leu | Met | Thr | Tyr | Cys | Asp | Ala | His |

```
                      3 5                              4 0                                 4 5
        Ala  Cys  Glu  Asp  Pro  Leu  Ile  Thr  Pro  Val  Pro  Thr  Ser  Glu  Asn  Pro
             50                           55                      60

Phe  Arg  Glu  Lys  Lys  Phe  Phe  Cys  Ala  Leu  Leu
        65                      70                      75
```

( 2 ) INFORMATION FOR SEQ ID NO:8:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 163118

( x i ) SEQUENCE DESCRIPTION: SEQ ID NO:8:

```
        Met  Ser  Ala  Thr  Asn  Asn  Ile  Ala  Gln  Ala  Arg  Lys  Leu  Val  Glu  Gln
        1                   5                        10                       15

Leu  Arg  Ile  Glu  Ala  Gly  Ile  Glu  Arg  Ile  Lys  Val  Ser  Lys  Ala  Ser
                       20                       25                     30

Ser  Glu  Leu  Met  Ser  Tyr  Cys  Glu  Gln  His  Ala  Arg  Asn  Asp  Pro  Leu
                  35                            40                     45

Leu  Val  Gly  Val  Pro  Ala  Ser  Glu  Asn  Pro  Phe  Lys  Asp  Lys  Lys  Pro
             50                            55                     60

Cys  Ile  Ile  Leu
        65
```

( 2 ) INFORMATION FOR SEQ ID NO:9:

( i ) SEQUENCE CHARACTERISTICS:
        ( A ) LENGTH: 136 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: CARDNOT01
        ( B ) CLONE: 183288

( x i ) SEQUENCE DESCRIPTION: SEQ ID NO:9:

```
CCGGGGCTAG CGCGAGGTCC TGCAGCGCTT GGTAGAGCAG CTCAAGTTGG AGGCTGGCGT     60

GGAGAGGNTC AAGGTCTCTC AGGCAGCTGC AGAGCTTCAA CAGTACTGTA TGCAGAATGC    120

CTGCAAGGAT GCCCTG                                                    136
```

( 2 ) INFORMATION FOR SEQ ID NO:10:

( i ) SEQUENCE CHARACTERISTICS:
        ( A ) LENGTH: 222 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: SPLNNOT02
        ( B ) CLONE: 206842

( x i ) SEQUENCE DESCRIPTION: SEQ ID NO:10:

AATATTCAAG AGAGCTACAT TTGAAGCCTG TACAAAAGCT TATCCCTGTA ACACATGTGC 60

CATAATATAC AAACTTCTAC TTTCGTCAGT CCTTAACATC TACCTCTCTG AATTTTCATG 120

AATTTCTATT TCACAAGGGT AATTGTTTTA TATACACTGG CAGCAGCNTN CAATAAAACT 180

TNGNNTGNAA ACTTTNAAAA NTAAAAANTA AAAAACTCGG GG 222

( 2 ) INFORMATION FOR SEQ ID NO:11:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: SPLNNOT02
        ( B ) CLONE: 211765

( x i ) SEQUENCE DESCRIPTION: SEQ ID NO:11:

ATTATTCAAG AGAGCTACAT TTGAGGCCTG TACAAAAGCT TATCCCTGTA ACACATGTGC 60

CATAATATAC AAACTTCTAC TTTNGTCAGT CCTTAACATC TACCTCTNTG ANTTNCATG 120

ANTNTNTATT TCACAAGGGT AATNGTTTTA TATACACTGG CAGCAGCATA CAATAAAACT 180

TAGTATGAAA CTTT 194

( 2 ) INFORMATION FOR SEQ ID NO:12:

( i ) SEQUENCE CHARACTERISTICS:
        ( A ) LENGTH: 221 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: STOMNOT01
        ( B ) CLONE: 215213

( x i ) SEQUENCE DESCRIPTION: SEQ ID NO:12:

GTTGCAGCAG GATAGTAATG ATGACACTGA AGATGTTTCA CTGTTGATG CGGAAGAGGA 60

GACGACTAAT AGACCAAGAA AAGCCAAAAT CAGACATCCA GTAGCATCGT TTTTCCACTT 120

ATTCTTTCGA GTCAGTGCAA TCATCGTCTA TCTTCTCTGT NAGTTGCTCA GCAGCAGCTT 180

TATTACCTGT ATGGTGACAA TTATCTTGTT GTTGTCGTGT T 221

( 2 ) INFORMATION FOR SEQ ID NO:13:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: STOMNOT01
        ( B ) CLONE: 215233

( x i ) SEQUENCE DESCRIPTION: SEQ ID NO:13:

GTTGCAGCAG GATAGTAATG ATGACACTGA AGATGTTTCA GCATTNCCAT GANTNCCTAT 60

TTCACAAGGG TAATTGTTTT ATATACACTG GCAGCAGCAT ANAATAAAAN TTAGTATGAA 120

ANTTTT 126

( 2 ) INFORMATION FOR SEQ ID NO:14:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: EOSIHET02
        ( B ) CLONE: 286874

( x i ) SEQUENCE DESCRIPTION: SEQ ID NO:14:

```
TCAAGTACAA ATCCCTTCAG ACCCCAGGAA AGTCTGTNCC TTTTTGTAGT AAAATGAATC      60
TTTCAAAGGT TTCCCAAACC ACTCCTTATG ATCCANTGAA TATTCAAGAG AGNTACATTT     120
GANGCCTGTA CAAAAGCTTA TCCCTGTAAC ANATGTGCCA TAATATACAA ACTTCTACTT     180
TNGTCAGTCC TTAACATCTA CCTCTCTGAN TTTNCATGAN TTTNTATTTC ACAAGGGTAA     240
TTGTTTTATA TACACTGGCA GCAGCATACA ATAAAACTTA GTATGAAACT TT             292
```

( 2 ) INFORMATION FOR SEQ ID NO:15:

( i ) SEQUENCE CHARACTERISTICS:
        ( A ) LENGTH: 356 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: TMLR3DT1
        ( B ) CLONE: 292714

( x i ) SEQUENCE DESCRIPTION: SEQ ID NO:15:

```
GGNCTCCTCC AGACGTCGAN CGACTATGAA GNAAAGTGGT TCAACAGCTC CGGCTGGAGG      60
CCGGACTCAA CCGCGTAAAA NTTTCCCAGG CAGCTGCAGA CTTGAAACAG TTCTGTCTGC     120
AGAATGCTCA ACATGACCCT CTGCTGACTG GAGTATNTTC AAGTACAAAT CCCTTCAGAC     180
CCCAGAAAGT CTGTNCCTTT TTGTAGTAAA ATGAATCTTT CAAAGGTTTC CCAAACCACT     240
CCTTATGATC CAGTGAATAT TCAAGAGAGC TACATTTGAA GCCTGTACAA AAGCTTATCC     300
CTGTAACACA TGTGCCATAA TATACAAACT TCTTCTTTCG TCAGTCCTTA ACATCT         356
```

( 2 ) INFORMATION FOR SEQ ID NO:16:

( i ) SEQUENCE CHARACTERISTICS:
        ( A ) LENGTH: 230 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: LVENNOT01
        ( B ) CLONE: 352443

( x i ) SEQUENCE DESCRIPTION: SEQ ID NO:16:

```
GTTCAACAGC TCCGGCTGGA GGCCGGACTC AACCGCGTAA AAGTTTCCCA GGCAGCTGCA      60
GACTTGAAAC AGTTCTGTCT GCAGAATGCT CAACATGACC CTCTGCTGAC TGGAGTATCT     120
TCAAGTACAA ATCCCTTCAG ACCCCAGAAA GTCTGTTCCT TTTTNTAGTA AAATGAATCT     180
```

```
TTCAAAGGTT  TCCCAAACCA  CTCCTTATGA  TCCAGTGAAT  ATTCAAGAGG                 230
```

( 2 ) INFORMATION FOR SEQ ID NO:17:

( i ) SEQUENCE CHARACTERISTICS:
        ( A ) LENGTH: 248 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: TMLR3DT1
        ( B ) CLONE: 404483

( x i ) SEQUENCE DESCRIPTION: SEQ ID NO:17:

```
GGCTNCTTCA  GCGTCGGCGN  TATGAAGAAA  GTGGTTCAAC  ANCTTCGGCT  NGAGGCCCGA      60
CTTAACCGCG  TAAAAGTTTC  CCAGGGAACT  NCAGACTTGA  AACAGTCTGT  CTGCAGAATG     120
CTCAACATGA  CCCTCTGCTG  ACTNGGGTAT  CTTCAAGTAC  AAATCCCTTC  AGACCCCAGA     180
AAGTCTGTTC  CNTTTTGTAG  TAAAATGAAT  CTTTCAAAGG  TTTTCCAAAC  CATTCTTATG     240
ATCCCGTG                                                                   248
```

( 2 ) INFORMATION FOR SEQ ID NO:18:

( i ) SEQUENCE CHARACTERISTICS:
        ( A ) LENGTH: 184 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: BLADNOT01
        ( B ) CLONE: 427016

( x i ) SEQUENCE DESCRIPTION: SEQ ID NO:18:

```
TCAAGGTCTC  TCAGGCAGCT  GCAGAGCTTC  AACAGTACTG  TATGCAGAAT  GCCTGCAAGG      60
ATGCCCTGCT  GGTGGGTGTT  CCAGCTGGAA  GTAACCCCTT  CCGGGAGCCT  AGATCCTGTG     120
CTTTACTCTG  AAGACTCTAG  GAGAGAAGTT  TGCTGAGGAA  TGCCTTCAAG  CACAAAGTGA     180
TGGG                                                                       184
```

( 2 ) INFORMATION FOR SEQ ID NO:19:

( i ) SEQUENCE CHARACTERISTICS:
        ( A ) LENGTH: 233 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THYRNOT01
        ( B ) CLONE: 433742

( x i ) SEQUENCE DESCRIPTION: SEQ ID NO:19:

```
CGCCGCCGCC  ATGTCCTCCG  GGGCTAGCGC  GAGGCCCTGC  AGCGCTTGGT  AGAGCAGCTC      60
AAGTTGGAGG  CTGGCGTGGA  GAGGATCAAG  GTCTCTCAGG  CAGCTGCAGA  GCTTCAACAG     120
TACTGTATGC  AGAATGCCTG  CAAGGATGCC  CTGCTGGTGG  GTGTTCCAGC  TGGAAGTAAC     180
CCCTTCCGGG  AGCCTAGATC  CTGTGCTTTA  CTCTGAAGAC  TCTAGGAGAG  AAG            233
```

( 2 ) INFORMATION FOR SEQ ID NO:20:

( i ) SEQUENCE CHARACTERISTICS:
        ( A ) LENGTH: 230 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THYRNOT01
        ( B ) CLONE: 439616

( x i ) SEQUENCE DESCRIPTION: SEQ ID NO:20:

```
TGGAGGCCGG ACTCAACCGC GTAAAAGTTT CCCAGGCAGC TGCAGACTTG AAACAGTTCT    60
GTCTGCAGAA TGCTCAACAT GACCCTCTGC TGACTGGAGT ATCTTCAAGT ACAAATCCCT   120
TCAGACCCCA GAAAGTCTGT TCCTTTTTGT AGTAAAATGA ATCTTTCAAA GGTTTCCCAA   180
ACCACTCCTT ATGATCCAGT GAATATTCAA GAGAGCTACA TTTGAAGCCT              230
```

( 2 ) INFORMATION FOR SEQ ID NO:21:

( i ) SEQUENCE CHARACTERISTICS:
        ( A ) LENGTH: 219 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: TLYMNOT2
        ( B ) CLONE: 453899

( x i ) SEQUENCE DESCRIPTION: SEQ ID NO:21:

```
AAAGTTCGGA GCCCTGCCCC NGCCGCGCGC CGCTGAGTTG TCTGGCCCCG CCGACCCACG    60
GCCCACGACC CACCGACCCA CGAATCGGCC CGGNCGTCGN GTGCANNATG TCTGGNTCCT   120
NCAGCGTCGC CGCTATGAAG AAAGTGGTTC AACAGCTCCG NNTGGNGGCC GGACTGAANC   180
GCGTAAAAGT TTGCCAGGGA GCTGCAGACT TGNAACAGT                          219
```

( 2 ) INFORMATION FOR SEQ ID NO:22:

( i ) SEQUENCE CHARACTERISTICS:
        ( A ) LENGTH: 241 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: KERANOT01
        ( B ) CLONE: 460437

( x i ) SEQUENCE DESCRIPTION: SEQ ID NO:22:

```
CGCCGACCCA CGGNCCACGN CCCACCGACC CACGNATCGG CCCGGCCGTC GCGTGCANCA    60
TGTCTGGCTC CTCCAGCGTC GCCGNTATGA AGAAAGTGGT TCAANAGCTC CGGCTGGAGG   120
CCGGACTCAA CCGCGTAAAA GTTTCCCAGG NAGCTGCAGA CTTGAAACAG TTCTGTCTGC   180
AGAATGNTCA ACATGACCCT CTGNTGACTG GAGTATCTTC AAGTACAAAT CCCTTCAGAC   240
C                                                                   241
```

( 2 ) INFORMATION FOR SEQ ID NO:23:

( i ) SEQUENCE CHARACTERISTICS:

( A ) LENGTH: 275 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: MMLR2DT1
( B ) CLONE: 475026

( x i ) SEQUENCE DESCRIPTION: SEQ ID NO:23:

| | | | | | | |
|---|---|---|---|---|---|---|
| GGCCCGGCCG | TCGCGTGCAC | CATGTCTGGG | TCCTNCAGCG | TCGCCGCTAT | GAAGAAAGTG | 60 |
| GTTCAACAGC | TCCGGCTGGA | GGCCGGACTN | AACCGCGTAA | AAGTTTNCCA | GGNAGNTGCA | 120 |
| GACTTGAAAC | AGTTCTGTNT | GCAGAATGCT | CAACATGACC | CTCTGCTGAC | TGGAGTATCT | 180 |
| TCAAGTACAA | ATCCCTTCAG | ACCCCAGAAA | GTNTGTTCCT | TTTTGTAGTA | AAATGAATCT | 240 |
| TTCAAAGGTT | TTCCAAACCA | NTNCTTATGA | TCCAG | | | 275 |

( 2 ) INFORMATION FOR SEQ ID NO:24:

( i ) SEQUENCE CHARACTERISTICS:
( A ) LENGTH: 216 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: HNT2RAT01
( B ) CLONE: 482881

( x i ) SEQUENCE DESCRIPTION: SEQ ID NO:24:

| | | | | | | |
|---|---|---|---|---|---|---|
| AGGAGCCCAG | CGGCCGNNGG | CCATTTCTCC | NGGGTTAANG | GGGGGNCCCN | NAAAAATTTT | 60 |
| TGGGGAGATC | AAAATTGAGG | GTTGNGTNGA | GAGGATCAAG | GTCTCTCAGG | CAGCTGCAGA | 120 |
| GCTTCAANAG | TANTGTATGC | AGAATGCCTG | CAAGGATGCC | CTGCTGGTGG | GTGTTCCAGC | 180 |
| TGGAAGTAAN | CCNTTNCGGG | AGCCTAGATN | CTGTGC | | | 216 |

( 2 ) INFORMATION FOR SEQ ID NO:25:

( i ) SEQUENCE CHARACTERISTICS:
( A ) LENGTH: 179 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: HNT2RAT01
( B ) CLONE: 484339

( x i ) SEQUENCE DESCRIPTION: SEQ ID NO:25:

| | | | | | | |
|---|---|---|---|---|---|---|
| CGNCGCCGCC | ATGTCCTCNG | GGGNTAGCGN | GAGGCCCTGC | AGCGCTTGGT | AGAGCAGCTC | 60 |
| AAGTTGGAGG | NTGGCGTGGA | GAGGATCAAG | GTCTCTCAGG | CAGCTGCAGA | GCTTCAACAG | 120 |
| TANTGTATGC | AGAATGCCTG | CAAGGNTGCC | CTGCTGGTGG | GTGTTCCAGC | TGGAAGTAA | 179 |

( 2 ) INFORMATION FOR SEQ ID NO:26:

( i ) SEQUENCE CHARACTERISTICS:
( A ) LENGTH: 261 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
    ( A ) LIBRARY: NEUTLPT01
    ( B ) CLONE: 498118

( x i ) SEQUENCE DESCRIPTION: SEQ ID NO:26:

```
CTGGCCCCGC CGACCCACGG CCCACGACCC ACCGACCCAC GAATNGGCCC GGCCGTCGCG      60
TGCACCATGT CTGGCTCCTC CAGCGTCGNC GNTATGAAGA AAGTGGTTCA ACAGCTCCGG     120
CTGGAGGCCG GACTCAACCG CGTAAAAGTT TCCCAGGCAG CTGCAGACTT GAAACAGTTN     180
TGTNTGCAGA ATGNTCAACA TGACCNTGTG CTGACTGGAG TATCTTCAAG TACAAATCCC     240
TTCAGACCCC AGAAAGTNTG T                                               261
```

( 2 ) INFORMATION FOR SEQ ID NO:27:

( i ) SEQUENCE CHARACTERISTICS:
        ( A ) LENGTH: 193 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: NEUTLPT01
        ( B ) CLONE: 498822

( x i ) SEQUENCE DESCRIPTION: SEQ ID NO:27:

```
CCCGGCCGTC GCGTGCACCA TGTCTGGCTC CTCCAGCGTC GCCGCTATGA AGAAAGTGGT      60
TCAACAGCTC CGGCTGGAGG CCGGACTCAA CCGCGTAAAA GTTCCCAGG CAGCTGCAGA      120
CTTGAAACAG TTCTGTCTGC AGAATGCTCA ACATGACCCT CTGCTGACTG GAGTATCTTC     180
AAGTACAAAT CCC                                                        193
```

( 2 ) INFORMATION FOR SEQ ID NO:28:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: NEUTLPT01
        ( B ) CLONE: 499687

( x i ) SEQUENCE DESCRIPTION: SEQ ID NO:28:

```
CTATTTCACA AGGGTAATTG TTTTATATAC ACTGGCAGCA GCATACAATA AAACTTAGTA      60
TGAAAC                                                                 66
```

( 2 ) INFORMATION FOR SEQ ID NO:29:

( i ) SEQUENCE CHARACTERISTICS:
        ( A ) LENGTH: 206 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: NEUTLPT01
        ( B ) CLONE: 500281

( x i ) SEQUENCE DESCRIPTION: SEQ ID NO:29:

| | | | | | | |
|---|---|---|---|---|---|---|
| GCCGGACTTA | ACCGCGTAAA | AGTTTNCCAG | GGAGCTNCAG | ACTTGAAACA | GTTCTGTCTN | 60 |
| CAGAATGCTC | AACATGACCC | TCTGCTGACT | GGAGTATCTT | CAAGTACAAA | TCCCTTCAGA | 120 |
| CCCCAGAAAG | TCTGTTCCNT | TTTGTAGTAA | AATGAATCTT | TCAAGGTTT | TCCAAACCAC | 180 |
| TCTTATGATC | CNGTGGATAT | TNAANG | | | | 206 |

( 2 ) INFORMATION FOR SEQ ID NO:30:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: MMLR3DT01
        ( B ) CLONE: 567503

( x i ) SEQUENCE DESCRIPTION: SEQ ID NO:30:

| | | | | | | |
|---|---|---|---|---|---|---|
| CGCGCCGCTG | AGTTGTCTGG | CCCCGNCGAC | CCACGGCCCA | CGACCCACCG | ACCCACGAAT | 60 |
| CGGCCCGGCC | GTNGCGTGCA | CCATGTCTGG | NTNCTNCAGC | GTCGCCGGTA | TGAAGAAAGT | 120 |
| GGTTCAACAG | CTCCGGCTGG | AGGCCGGACT | NAACCGCGTA | AAAGTTTCCC | AGGCAGCTGC | 180 |
| AGACTTGAAA | CAGTTCTGTC | TGCAGAATGN | TCAACATGAC | CCTNTGNTGA | CTGGAGTATC | 240 |
| TTCAAGTACA | AATCCCTTCA | GACCCCAGAA | AGTNTGT | | | 277 |

( 2 ) INFORMATION FOR SEQ ID NO:31:

( i ) SEQUENCE CHARACTERISTICS:
        ( A ) LENGTH: 260 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: UTRSNOT01
        ( B ) CLONE: 586994

( x i ) SEQUENCE DESCRIPTION: SEQ ID NO:31:

| | | | | | | |
|---|---|---|---|---|---|---|
| GCGCCGCTGA | GTTGTCTGGC | CCGGCCGACC | CACGGNTCAC | GACCCACCGA | CCCACGAATC | 60 |
| GGCCCGGCCG | TCGNGTGCAC | CATGTCTGGN | TNCTTCAGCG | TCGGCGGTAT | GAAGAAAGTG | 120 |
| GTTCAACAGC | TTCGGNTGGA | GGCCGGACTT | AACCGCGTAA | AAGTTTCCA | GGGAGCTGCA | 180 |
| GACTTGAAAC | AGTTCTGTCT | GCAGAATGTT | AACATGACCC | TNTGNTGANT | TGAGTATTTN | 240 |
| AAGTACAAAT | CCTTNAGANC | | | | | 260 |